US012545936B2

(12) United States Patent
Kotagiri et al.

(10) Patent No.: US 12,545,936 B2
(45) Date of Patent: Feb. 10, 2026

(54) EXPRESSION AND SECRETION OF UV ABSORBENT MATERIAL FROM TRANSFORMED BACTERIA

(71) Applicant: University of Cincinnati, Cincinnati, OH (US)

(72) Inventors: Nalinikanth Kotagiri, West Chester, OH (US); Tushar Madaan, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 17/674,161

(22) Filed: Feb. 17, 2022

(65) Prior Publication Data

US 2022/0275411 A1 Sep. 1, 2022

Related U.S. Application Data

(60) Provisional application No. 63/150,137, filed on Feb. 17, 2021.

(51) Int. Cl.
*C12P 13/04* (2006.01)
*A61K 8/99* (2017.01)
*A61Q 17/00* (2006.01)

(52) U.S. Cl.
CPC ................ *C12P 13/04* (2013.01); *A61K 8/99* (2013.01); *A61Q 17/00* (2013.01)

(58) Field of Classification Search
CPC .......... C12P 13/04; C12P 13/005; A61K 8/99; A61Q 19/00; A61Q 17/00
See application file for complete search history.

(56) References Cited

FOREIGN PATENT DOCUMENTS

WO WO-2017185018 A1 * 10/2017 ............. A61K 35/74

OTHER PUBLICATIONS

Burkovski, A; Kramer, R., "Bacterial amino acid transport proteins: occurrence, functions, and significance for biotechnological applications" Appl Microbiol Biotechnol (2002) 58:265-274 DOI 10.1007/s00253-001-0869-4. Springer-Verlag. Dec. 21, 2001.
Byrd, A; Belkaid, Y; Segre, J., "The human skin microbiome" Nature Reviews, Microbiology. vol. 16. Mar. 2018.
Jayaraman, P; Devarajan, K; Chua, T; Zhang, H; Gunawan, E; Poh, C., "Blue light-mediated transcriptional activation and repression of gene expression in bacteria" Nucleic Acids Research, 2016, vol. 44, No. 14. Jun. 28, 2016. doi: 10.1093/nar/gkw548.
Mena, L; Rizk, P; Limas, D., "Bringing Light to Transcription: The Optogenetics Repertoire" Frontiers in Genetics. Nov. 2, 2018. doi: 10.3389/fgene.2018.00518.
Rost, B; Warme, F. S; Schmitz, D; Hegemann, P., "Optogenetic Tools for Subcellular Applications in Neuroscience" CellPress, Neuron Primer. https://doi.org/10.1016/j.neuron.2017.09.047.

* cited by examiner

*Primary Examiner* — Mary Maille Lyons
(74) *Attorney, Agent, or Firm* — DINSMORE & SHOHL LLP

(57) ABSTRACT

A genetically modified strain of commensal bacteria *Staphylococcus epidermidis* is provided which produces a material with UV absorbing properties. The material with UV absorbing properties may be a mycosporine-like amino acid such as shinorine.

12 Claims, 9 Drawing Sheets

Specification includes a Sequence Listing.

SEQUENCE LISTING

<160> NUMBER OF SEQ ID NOS: 9

<210> SEQ ID NO 1
<211> LENGTH: 1261
<212> TYPE: DNA
<213> ORGANISM: Anabaena variabilis

<400> SEQUENCE: 1
tgattaactt tataggaggt aaaaacatat gagtatcgtc caagcaaagt ttgaagctaa 60
ggaaacatct tttcatgtag aaggttacga aaagattgag tatgatttgg tgtatgtaga 120
tggtattttt gaaatccaga attctgcact agcagatgta tatcaaggtt ttggacgatg 180
cttggcgatt gtagatgcta acgtcagtcg gttgtatggt aatcaaattc aggcatattt 240
ccagtattat ggtatagaac tgaggctatt tcctattacc attactgaac cagataagac 300
tattcaaact ttcgagagag ttatagatgt ctttgcagat ttcaaattag tccgcaaaga 360
accagtatta gtcgtgggtg gcggtttaat tacagatgtt gtcggctttg cttgttctac 420
atatcgtcgc agcagcaatt acatccgcat tcctactaca ttgattggat taattgatgc 480
cagtgtagca attaaggtag cagttaatca tcgcaaactg aaaaaccgtt tgggtgctta 540
tcatgcttct cgcaaagtat ttttagattt ctccttgttg cgtactctcc ctacagacca 600
agtacgtaac gggatggcgg aattggtaaa aatcgctgta gtagcgcatc aagaagtttt 660
tgaattgttg gagaagtacg gcgaagaatt actacgtact cattttggca atatagatgc 720
aactccagag attaaagaaa tagcccatcg tttgacttac aaagctatcc ataagatgtt 780
ggaattggaa gttcccaacc tgcatgagtt agacctagat agggtgattg cttacggtca 840
cacttggagt cccaccttgg aacttgcgcc tcgtctaccc atgttccacg gacacgccgt 900
taatgtagat atggctttct cggcaacgat cgccgcccgt agaggatata ttacaattgc 960
agaacgcgat cgtattttag gattaatgag tcgcgttggt ctatccctcg accatcccat 1020
gttggatata gatattttgt ggcgtggtac tgaatctatc acattaactc gtgatggttt 1080
gttaagagct gctatgccaa aacccattgg tgattgtgtc ttcgtcaatg acctgacaag 1140
agaagaatta gcagccgcat tagctgacca caaagaactt tgtaccagtt atccccgtgg 1200
tggtgaaggt gtggatgtgt atcccgttta tcaaaaagaa ttaatcggga gtgttaaata 1260
a 1261

<210> SEQ ID NO 2
<211> LENGTH: 577
<212> TYPE: DNA
<213> ORGANISM: Anabaena variabilis

<400> SEQUENCE: 2
tgattaactt tataaggagg aaaaacatat gctttctggt catatcgaag gacaaacctt 60
aaagatgttt gttcacatga ccaaagctaa aaaagtctta gaaattggga tgtttaccgg 120
ttattcggcg ctggcgatgg cggaagcatt accagaggat ggactgcttg tggcttgtga 180
agttgaccct tacgcggcgg aaattggaca gaaagccttt caacaatctc cccacggtgg 240
aaagattcgt gtggaattgg atgcagcctt agcaactctt gataagttag cagaagctgg 300
ggagtctttt gacttggtat ttatcgacgc agataaaaaa gagtatgtag cctattttca 360
caagttgcta ggtagcagtt tgttagcacc agatggcttt atttgtgtag ataacacctt 420
attacaaggg gaagtttatc taccagcaga ggaacgtagc gtcaatggtg aagcgatcgc 480
gcaatttaat catacagtag ctatagaccc ccgtgtagaa caggttttgt tgccgttgcg 540
agatggttta acaattatcc gcagaataca accttaa 577

<210> SEQ ID NO 3
<211> LENGTH: 1405
<212> TYPE: DNA
<213> ORGANISM: Anabaena variabilis

<400> SEQUENCE: 3
tgattaactt tataaggagg aaaaacatat ggcacaatcc cttccccttt cttccgcacc 60
tgctacaccg tctcttcctt cccagacgaa aatagccgca attatccaaa atatctgcac 120
tttggctttg ttattactag cattgcccat taatgccacc attgttttta tatccttgtt 180
agtcttccga ccgcaaaagg tcaaagcagc aaacccccaa accattctta tcagtggcgg 240
taagatgacc aaagctttac aactagcaag gtcattccac gcggctggac atagagttgt 300
cttggtggaa acccataaat actggttgac tggtcatcgt tttcccaag cagtggataa 360 gttttacaca gtccccgcac cccaggacaa tccccaagct tacattcagg ctttggtaga 420
tatcgtcaaa caagaaaaca tcgatgttta tattcccgtc accagtccag tgggtagcta 480
ctacgactca ttagccaaac cagagttatc ccattattgc gaagtgtttc actttgacgc 540
agatattacc caaatgttgg atgataaatt tgcgttgaca caaaaagcgc gatcgcttgg 600
tttatcagta cccaaatcct ttaaaattac ctcaccagaa caagtcatca acttcgattt 660
ttctggagag acacgtaaat acatcctcaa aagcattccc tacgactcag tgcggcggtt 720
ggacttaacc aaactcccct gtgctactcc agaggaaaca gcagcattcg tcagaagttt 780
gccaattact cccgaaaaac cgtggattat gcaggaattt atccccggta aggaattctg 840
cacccatagc accgttcgga atggggaact cagactgcat tgctgttgcg aatcttcagc 900
cttccaagtt aattatgaga atgtaaataa cccgcaaatt accgaatggg tacagcattt 960

```
tgtcaaggaa ctgaaactga caggacagat ttcctttgac tttatccaag ccgaagacgg   1020
aacagtttac gccatcgagt gtaacccccg cacacattca gcaattacca cattttacga   1080
ccaccccccag gtagcagaag cgtacttgag tcaagcaccg acgactgaaa ccatacaacc  1140
actaacgaca agcaagccta cctattggac ttatcacgaa gtttggcgtt taactggtat   1200
ccgttctttc acccagttgc aaagatggct ggggaatatt tggcgcggga ctgatgcgat   1260
ttatcagcca gatgacccct taccgttttt gatggtacat cattggcaaa ttcccctact   1320
gttattgaat aatttgcgtc gtcttaaagg ttggacgcgg atagatttca atattgggaa   1380
gttggtggaa ttggggggag attag                                         1405
```

<210> SEQ ID NO 4
<211> LENGTH: 2672
<212> TYPE: DNA
<213> ORGANISM: Anabaena variabilis

<400> SEQUENCE: 4

```
atgcagacta tagattttaa tattcgtaag ttacttgtag agtggaacgc gacccacaga     60
gattatgatc tttcccagag tttacatgaa ctaattgtag ctcaagtaga acgaacacct    120
gaggcgatcg ctgtcacctt tgacaagcaa caactaactt atcaagaact aaatcataaa    180
gcaaaccagc taggacatta tttacaaaca ttaggagtcc agccagaaac cctggtaggc    240
gtttgtttag aacgttcctt agaaatggtt atctgtcttt taggaatcct caaagctggg    300
ggtgcttatg ttcctattga ccctgaatat cctcaagaac gcatagctta tatgctagaa    360
gattctcagg tgaaggtact actaactcaa gaaaaattac tcaatcaaat tccccaccat    420
caagcacaaa ctatctgtgt agatagggaa tgggagaaaa tttccacaca agctaatacc    480
aatcccaaaa gtaatataaa aacggataat cttgcttatg taatttacac ctctggttcc    540
actggtaaac caaaaggtgc aatgaacacc cacaaaggta tctgtaatcg cttattgtgg    600
atgcaggaag cttatcaaat cgattccaca gatagcattt tacaaaaaac cccctttagt    660
tttgatgttt ccgtttggga gttcttttgg actttattaa ctggcgcacg tttggtaata    720
gccaaaccag gcggacataa agatagtgct tacctcatcg atttaattac tcaagaacaa    780
atcactacgt tgcattttgt cccctcaatg ctgcaagtgt ttttacaaaa tcgccatgta    840
agcaaatgca gctctctaaa aagagttatt tgtagcggtg aagctttatc tatagattta    900
caaaatagat tttccagca tttgcaatgt gaattacata acctctatgg cccgacagaa      960
gcagcaattg atgtcacatt ttggcaatgt agaaaagata gtaatttaaa gagtgtacct   1020
attggtcgtc ccattgctaa tactcaaatt tatattcttg atgccgattt acaaccagta   1080
aatattggtg tcactggtga aatttatatt ggtggtgtag ggttgctcg tggttatttg    1140
aataaagaag aattgaccaa agaaaaattt attattaatc cctttcccaa ttctgagttt   1200
aagcgacttt ataaaacagg tgatttagct cgttatttac ccgatggaaa tattgaatat   1260
cttggtagaa cagattatca agtaaaaatt cggggttata gaattgaaat tggcgagatt   1320
gaaaatgttt tatcttcaca cccacaagtc agagaagctg tagtcatagc gcgggatgat   1380
aacgctcaag aaaaacaaat catcgcttat attacctata actccatcaa acctcagctt   1440
gataatctgc gtgatttcct aaaagcaagg ctacctgatt ttatgattcc agccgctttt   1500
gtgatgctgg agcatcttcc tttaactccc agtggtaaag tagaccgtaa ggcattacct   1560
aagcctgatt tatttaatta tagtgaacat aattcctatg tagcgcctcg gaatgaagtt   1620
gaagaaaaat tagtacaaat ctggtcgaat attctgcatt tacctaaagt aggtgtgaca   1680
```

gaaaactttt tcgctattgg tggtaattcc ctcaaagctc tacatttaat ttctcaaatt 1740
gaagagttat ttgctaaaga gatatcctta gcaacacttt taacaaatcc agtaattgca 1800
gatttagcca aggttattca agcaaacaac caaatccata attcacccct agttccaatt 1860
caaccacaag gtaagcagca gcctttcttt tgtatacatc ctgctggtgg tcatgtttta 1920
tgctatttta aactcgcaca atatatagga actgaccaac cattttatgg cttacaagct 1980
caaggatttt atggagatga agcacccttg acgcgagttg aagatatggc tagtctctac 2040
gtcaaaacta ttagagaatt tcaaccccaa gggccttatc gtgtcggggg gtggtcattt 2100
ggtggagtcg tagcttatga agtagcacag cagttacata gacaaggaca agaagtatct 2160
ttactagcaa tattagattc ttacgtaccg attctgctgg ataaacaaaa acccattgat 2220
gacgtttatt tagttggtgt tctctccaga gtttttggcg gtatgtttgg tcaagataat 2280
ctagtcacac ctgaagaaat agaaaattta actgtagaag aaaaaattaa ttacatcatt 2340
gataaagcac ggagcgctag aatattcccg cctggtgtag aacgtcaaaa taatcgccgt 2400
attcttgatg ttttggtggg aactttaaaa gcaacttatt cctatataag acaaccatat 2460
ccaggaaaag tcactgtatt tcgagccagg gaaaaacata ttatggctcc tgacccgacc 2520
ttagtttggg tagaattatt ttctgtaatg gcggctcaag aaattaagat tattgatgtc 2580
cctggaaacc attattcgtt tgttctagaa ccccatgtac aggttttagc acagcgttta 2640
caagattgtc tggaaaataa ttcatgactc ga 2672

<210> SEQ ID NO 5
<211> LENGTH: 12072
<212> TYPE: DNA
<213> ORGANISM: Staphylococcus epidermidis

<400> SEQUENCE: 5
cctttgcgaa agagttaata agttaacaga agatgaacca aaactaaatg gtttagcagg 60
aaacttagat aaaaaaatga atccagaatt atattcagaa caggaacagc aacaagaaca 120
acaaaagaat caaaaacgag atagaggtat gcacttatag aacatgcatt tatgccgaga 180
aaacttattg gttggaatgg gctatgtgtt agctaacttg ttagcgagtt ggttggactt 240
gaattgggat taatcccaag aaagtaccaa ctcaacaaca cataaagccc tgtaggttcc 300
gaccaataag gaaattggaa taaagcaata aaaggagttg aagaaatgaa attcagagaa 360
gcctttgaga attttataac aagtaagtat gtacttggtg ttttagtagt tttaactgtt 420
taccagataa tacaaatgct taaataaaaa aagacttgat ctgattagac caaatctttt 480
gatagtgtta tattaataac aaaataaaaa ggagtcgctc acgccctacc aaagtttgtg 540
aacgacatca ttcaaagaaa aaaacactga gttgttttta taatcttgta tatttagata 600
ttaaacgata tttaaatata catcaagata tatatttggg tgagcgatta cttaaacgaa 660
attgagatta aggagtcgat tttttatgta taaaaacaat catgcaaatc attcaaatca 720
tttggaaaat cacgatttag acaatttttc taaaaccggc tactctaata gccggttgga 780
cgcacatact gtgtgcatat ctgatccaaa attaagtttt gatgcaatga cgatcgttgg 840
aaatctcaac cgagacaacg ctcaagccct ttctaaattt atgagtgtag agccccaaat 900
aagactttgg gatattcttc aaacaaagtt taaagctaaa gcacttcaag aaaaagttta 960
tattgaatat gacaaagtga aagcagatag ttgggataga cgtaatatgc gtattgaatt 1020
taatccaaac aaacttacac gagatgaaat gatttggtta aaacaaaata taataagcta 1080

```
catggaagat gacggtttta caagattaga tttagccttt gattttgaag atgatttgag   1140
tgactactat gcaatgtctg ataaagcagt taagaaaact attttttatg gtcgtaatgg   1200
taagccagaa acaaaatatt ttggcgtgag agatagtaat agatttatta gaatttataa   1260
taaaaagcaa gaacgtaaag ataatgcaga tgctgaagtt atgtctgaac atttatggcg   1320
tgtagaaatc gaacttaaaa gagatatggt ggattactgg aatgattgct ttagtgattt   1380
acatatcttg caaccagatt ggaaaactat ccaacgcact gcggatagag caatagtttt   1440
tatgttattg agtgatgaag aagaatgggg aaagcttcac agaaattcta gaacaaaata   1500
taagaatttg ataaaagaaa tttcgccagt cgatttaacg gacttaatga aatcgacttt   1560
aaaagcgaac gaaaaacaat tgcaaaaaca aatcgatttt tggcaacatg aatttaaatt   1620
ttggaaatag tgtacatatt aatattactg aacaaaaatg atatatttaa actattctaa   1680
tttaggagga tttttttatg aagtgtctat ttaaaaattt ggggaattta tatgaggtga   1740
aagaataatt taccccctata aactttagtc acctcaagta aagaggtaaa attgtttagt   1800
ttatataaaa aatttaaagg tttgttttat agcgttttat tttggctttg tattctttca   1860
ttttttagtg tattaaatga aatggtttta aatgtttctt tacctgatat tgcaaatcat   1920
tttaatacta ctcctggaat tacaaactgg gtaaacactg catatatgtt aacttttttcg   1980
ataggaacag cagtatatgg aaaattatct gattatataa atataaaaaa attgttaatt   2040
attggtatta gtttgagctg tcttggttca ttgattgctt ttattgggcc cacctaggaa   2100
ttgaatgaga catgctacac ctccggataa taaatatata taaacgtata tagatttcat   2160
aaagtctaac acactagact tatttacttc gtaattaagt cgttaaaccg tgtgctctac   2220
gaccaaaact ataaaacctt taagaacttt cttttttttac aagaaaaaag aaattagata   2280
aatctctcat atcttttatt caataatcgc atccgattgc agtataaatt taacgatcac   2340
tcatcatgtt catatttatc agagctcgtg ctataattat actaatttta taaggaggaa   2400
aaaatatggg catttttagt atttttgtaa tcagcacagt tcattatcaa ccaaacaaaa   2460
aataagtggt tataatgaat cgttaataag caaaattcat ataaccaaat taaagagggt   2520
tataatgaac gagaaaaata taaaacacag tcaaaacttt attacttcaa aacataatat   2580
agataaaata atgacaaata taagattaaa tgaacatgat aatatctttg aaatcggctc   2640
aggaaaaggc cattttaccc ttgaattagt aaagaggtgt aatttcgtaa ctgccattga   2700
aatagaccat aaattatgca aaactacaga aaataaactt gttgatcacg ataatttcca   2760
agttttaaac aaggatatat tgcagtttaa atttcctaaa aaccaatcct ataaaatata   2820
tggtaatata ccttataaca taagtacgga tataatacgc aaaattgttt ttgatagtat   2880
agctaatgag atttatttaa tcgtggaata cgggtttgct aaaagattat taaatacaaa   2940
acgctcattg gcattacttt taatggcaga agttgatatt tctatattaa gtatggttcc   3000
aagagaatat tttcatccta aacctaaagt gaatagctca cttatcagat taagtagaaa   3060
aaaatcaaga atatcacaca aagataaaca aaagtataat tatttcgtta tgaaatgggt   3120
taacaaagaa tacaagaaaa tatttacaaa aaatcaattt aacaattcct taaaacatgc   3180
aggaattgac gatttaaaca atattagctt tgaacaattc ttatctcttt tcaatagcta   3240
taaattattt aataagtaag ttaagggatg cataaactgc atcccttaac ttgtttttcg   3300
tgtgcctatt ttttgtgaat cgattatgtc ttttgcgcag tcggcttaaa ccagttttcc   3360
gcggcgctcg agcggccgca tagttaagcc agccccgaca cccgccaaca cccgctgacg   3420
cgccctgacg ggcttgtctg ctcccggcat ccgcttacag acaagctgtg accgtctccg   3480
```

```
ggagctgcat gtgtcagagg ttttcaccgt catcaccgaa acgcgcgaga cgaaagggcc   3540
tcgtgatacg cctattttta taggttaatg tcatgataat aatggtttct tagacgtcag   3600
gtggcacttt tcggggaaat gtgcgcggaa cccctatttg tttatttttc taaatacatt   3660
caaatatgta tccgctcatg agacaataac cctgataaat gcttcaataa tattgaaaaa   3720
ggaagagtat gagtattcaa catttccgtg tcgcccttat tccctttttt gcggcatttt   3780
gccttcctgt ttttgctcac ccagaaacgc tggtgaaagt aaaagatgct gaagatcagt   3840
tgggtgcacg agtgggttac atcgaactgg atctcaacag cggtaagatc cttgagagtt   3900
ttcgccccga agaacgtttt ccaatgatga gcacttttaa agttctgcta tgtggcgcgg   3960
tattatcccg tattgacgcc gggcaagagc aactcggtcg ccgcatacac tattctcaga   4020
atgacttggt tgagtactca ccagtcacag aaaagcatct tacggatggc atgacagtaa   4080
gagaattatg cagtgctgcc ataaccatga gtgataacac tgcggccaac ttacttctga   4140
caacgatcgg aggaccgaag gagctaaccg cttttttgca caacatgggg gatcatgtaa   4200
ctcgccttga tcgttgggaa ccggagctga atgaagccat accaaacgac gagcgtgaca   4260
ccacgatgcc tgtagcaatg gcaacaacgt tgcgcaaact attaactggc gaactactta   4320
ctctagcttc ccggcaacaa ttaatagact ggatggaggc ggataaagtt gcaggaccac   4380
ttctgcgctc ggcccttccg gctggctggt ttattgctga taaatctgga gccggtgagc   4440
gtgggtctcg cggtatcatt gcagcactgg ggccagatgg taagccctcc cgtatcgtag   4500
ttatctacac gacggggagt caggcaacta tggatgaacg aaatagacag atcgctgaga   4560
taggtgcctc actgattaag cattggtaac tgtcagacca agtttactca tatatacttt   4620
agattgattt aaaacttcat ttttaattta aaaggatcta ggtgaagatc ctttttgata   4680
atctcatgac caaaatccct taacgtgagt tttcgttcca ctgagcgtca gaccccgtag   4740
aaaagatcaa aggatcttct tgagatcctt tttttctgcg cgtaatctgc tgcttgcaaa   4800
caaaaaaacc accgctacca gcggtggttt gtttgccgga tcaagagcta ccaactcttt   4860
ttccgaaggt aactggcttc agcagagcgc agataccaaa tactgttctt ctagtgtagc   4920
cgtagttagg ccaccacttc aagaactctg tagcaccgcc tacatacctc gctctgctaa   4980
tcctgttacc agtggctgct gccagtggcg ataagtcgtg tcttaccggg ttggactcaa   5040
gacgatagtt accggataag gcgcagcggt cgggctgaac ggggggttcg tgcacacagc   5100
ccagcttgga gcgaacgacc tacaccgaac tgagatacct acagcgtgag ctatgagaaa   5160
gcgccacgct tcccgaaggg agaaaggcgg acaggtatcc ggtaagcggc agggtcggaa   5220
caggagagcg cacgagggag cttccagggg gaaacgcctg gtatctttat agtcctgtcg   5280
ggtttcgcca cctctgactt gagcgtcgat ttttgtgatg ctcgtcaggg gggcggagcc   5340
tatggaaaaa cgccagcaac gcggcctttt tacggttcct ggccttttgc tggccttttg   5400
ctcacatgtt ctttcctgcg ttatcccctg attctgtgga taaccgtatt accgcctttg   5460
agtgagctgg cggccgctgc atgcctgcag gtcgactcta gaggatcccc cccctgatat   5520
ttttgactaa accaaatgct aacccagaaa tacaatcact gtgtctaatg aataatttgt   5580
tttataaaca ctttttttgtt tacttctcat ttttaattag ttataattaa ctaaataata   5640
gagcattaaa tatatttaat aaaacttatt taatgcaaaa ttatgactaa catatctata   5700
ataaataaag attagatatc aatatattat cgggcaaatg tatcgagcaa gatgcatcgg   5760
atcgatccag gaggtatacc tgattaactt tataaggagg aaaaacatat gagtatcgtt   5820
```

caagcgaaat ttgaagcaaa agaaacgagt ttccatgtgg aaggatatga gaagatcgag 5880
tacgatttgg tgtatgttga cggcattttt gagatacaaa attctgcgtt ggcggatgta 5940
tatcagggat ttggtagatg cttggcgata gttgatgcga atgtgagtcg tttgtatggt 6000
aatcagatcc aggcgtattt ccaatactat ggtattgagt tacgtttgtt tcctataacg 6060
attacggagc ctgataagac gattcagact ttcgagcgag ttattgacgt ctttgctgac 6120
ttcaagttag tcagaaaaga accagtcttg gtagtgggtg gtggattaat cacagacgta 6180
gtaggcttcg cgtgcagtac ttacagaaga tcttctaact acatccgaat accgacaacg 6240
ttaataggtt tgattgatgc tagtgttgct atcaaggtgg cagtaaatca cagaaaatta 6300
aagaaccgat tgggagctta ccacgcatca cgaaaagtct tcttagactt ttctttgtta 6360
cgaacattgc cgactgatca agtcagaaac ggaatggctg aattagtaaa gatcgcggtc 6420
gtggcacatc aggaggtgtt cgagttgtta gagaagtacg gagaagagtt attacgaacg 6480
catttcggta atatagacgc tactcctgaa attaaggaga tcgcgcaccg attgacatac 6540
aaagctattc ataagatgtt agagttggag gttcctaact tacacgagtt ggacttagac 6600
cgtgtaatag cttatggtca tacgtggagt ccgacattag aattggctcc tcgtttgcct 6660
atgttccacg gacacgcggt caacgtcgat atggcattca gtgcgacgat tgctgcacga 6720
cgaggttaca ttacgattgc tgagcgtgat agaatcttag gattaatgag tcgagtcggt 6780
ttaagtttgg accaccctat gttggatatt gacatcttat ggcgaggtac agaatctatc 6840
actttaactc gagacggatt attgcgtgct gcaatgccga agcctatagg cgactgtgta 6900
ttcgtcaatg atttgactcg agaagaattg gcagcagcgt tagcggacca caaagaatta 6960
tgtacgagtt atccgcgtgg tggtgaaggc gtcgatgtct atccagtata tcaaaaagag 7020
ttaatcggaa gtgtaaagta acccccctga ttaactttat aaggaggaaa aacatatgtt 7080
atcaggacat attgaaggac aaactttaaa gatgtttgtt catatgacga aggctaagaa 7140
ggtattagaa attggaatgt tcacaggcta ctctgcgtta gcgatggcag aggcgttacc 7200
agaggatggt ttgttagtcg cgtgcgaagt tgatccttac gcagcggaga taggtcaaaa 7260
ggcattccag caatcaccac acggcggcaa gatacgagtt gagttggacg cagctttagc 7320
gactttggac aaattagcag aagcaggaga gagttttgat ttggttttca tagacgctga 7380
caagaaggaa tacgtggctt attttcataa gttgttggga agttcattat tagctccaga 7440
cggtttcata tgcgttgaca acactttgtt gcaaggagaa gtatatttac cggcggagga 7500
gcgatcagtg aatggtgagg ctatcgcaca gttcaatcat actgtcgcaa ttgatccgcg 7560
agtcgagcaa gtgttattgc cgttgagaga tggtttaact attattcgtc gtattcagcc 7620
ataacccccc tgattaactt tataaggagg aaaaacatat ggctcaatct ttaccattat 7680
cttctgcacc agcgactccg tcattgccat cacagactaa gattgctgcg atcatccaga 7740
atatctgtac gttggcgttg ttgttgttgg ctttgccaat taacgctacg atagtgttta 7800
tcagtttgtt agtatttcga ccacagaagg tgaaggctgc taacccacaa acaatattaa 7860
tctcaggtgg aaagatgact aaagcattgc agttagcacg atctttccat gcagctggtc 7920
atagagttgt tttggtggaa acgcataagt attggttgac tggtcacaga ttctcacagg 7980
cagtagacaa attttatact gtccctgcac cgcaagacaa tccgcaagcg tatattcaag 8040
ctttggtaga cattgtcaaa caggaaaata tagacgtcta tattccggtg acatctccgg 8100
tcggctcata ttacgattca ttggcgaagc cggaattgtc tcactattgt gaagtgtttc 8160
acttcgatgc agacataaca caaatgttag acgacaaatt tgctttaact caaaaagcac 8220
gatctttggg cttgtcagtc ccgaagtctt tcaaaataac ttctccggag caagtaatta 8280
acttcgactt ctcaggagaa actagaaaat acatcttaaa aagtattcca tacgacagtg 8340
tacgtcgttt agatttgaca aagttacctt gtgctacgcc ggaagagaca gcagctttcg 8400
ttagaagttt gccgatcacg ccagagaagc cgtggataat gcaggaattt ataccaggca 8460
aggaattttg tacacactca actgtcagaa acggagaatt acgtttgcac tgctgttgtg 8520
agtcatcagc tttccaagtc aactatgaga acgtaaacaa tccgcagata acagaatggg 8580
tccaacattt tgtcaaagag ttaaagttga ctggacaaat ctctttcgat ttcatacaag 8640
ctgaagatgg aacagtatac gctattgagt gtaaccctcg aactcattca gcgataacta 8700
ctttctatga ccatccgcaa gttgcagaag cttacttgtc acaggctcca acaacggaga 8760
caattcaacc attaacaaca tctaaaccaa cttattggac atatcatgaa gtgtggagat 8820
taacgggtat ccgaagtttc actcagttgc aacgatggtt gggcaacatt tggcgtggca 8880
ctgatgcgat ttaccaaccg gacgacccgt tacctttctt gatggttcat cattggcaaa 8940
ttccgttgtt attgttgaat aatttgcgac gattaaaggg ttggacacgt attgatttca 9000
acattggaaa attggtcgaa ttaggaggtg actagccccc ctgattaact ttataaggag 9060
gaaaaacata tgcagacgat tgattttaat atccgaaagt tgttagtgga atggaacgcg 9120
acacatcgtg attacgactt gtcacagtct ttgcacgaat tgatagttgc acaagttgaa 9180
agaactcctg aagctattgc tgttacgttc gacaagcagc aattaacgta tcaggaatta 9240
aatcataaag cgaaccagtt gggacactac ttacaaacgt taggtgtcca accggagacg 9300
ttagtcggtg tctgtttgga acgtagtttg gagatggtca tttgtttatt aggaatattg 9360
aaggcgggcg gtgcttatgt ccctatcgac ccggaatatc ctcaggaacg tatagcttac 9420
atgttagaag actctcaggt gaaggttttg ttgactcaag aaaaattatt aaatcagatc 9480
ccgcaccatc aggcacaaac aatatgtgtt gatagagaat gggagaaaat ctctacacaa 9540
gcgaatacaa atccgaaatc aaatattaag acggataact tggcatacgt catttacact 9600
tctggtagta caggaaaacc aaaaggtgcg atgaacacgc ataaaggcat atgtaatcga 9660
ttattgtgga tgcaagaggc ttatcagatc gatagtacgg acagtatctt gcaaaaaacg 9720
ccgttctctt ttgatgtttc agtctgggag tttttctgga cattattgac gggagcgcga 9780
ttggttatcg ctaagccagg aggccacaaa gacagtgcat atttgataga tttgataaca 9840
caggagcaaa ttacaacttt acactttgtg ccgtcaatgt tacaagtctt cttacagaac 9900
cgtcacgtaa gtaagtgtag ttctttaaag cgagtcattt gctcaggaga ggcgttatca 9960
attgatttac agaatagatt tttccaacac ttgcagtgtg agttgcacaa cttatatggt 10020
ccaacagaag ctgctattga cgtaactttt tggcaatgta gaaaggattc taatttaaaa 10080
tctgtcccga taggtagacc tatagcgaat acacaaatat atatcttgga cgctgattta 10140
cagccggtta acataggcgt aacgggagag atttatattg gaggtgtagg cgtggctcgt 10200
ggatatttga ataaagagga gttaactaaa gaaaaattca tcatcaatcc tttcccaaac 10260
tctgaattca aacgtttgta taaaacgggc gatttagcgc gttatttacc agacggcaac 10320
atagaatatt tgggcagaac agattatcaa gtgaaaatac gaggctatag aatagaaata 10380
ggcgaaatag agaacgtctt gtctagtcat ccacaggtga gagaagctgt cgtaatagct 10440
agagatgata acgcgcaaga gaaacagatc atcgcttaca tcacatataa tagtatcaag 10500
ccgcaattgg acaacttacg agacttcttg aaggcacgtt tgccggattt tatgattcct 10560
gcagcttttg tgatgttgga acacttaccg ttgactccaa gtggcaaagt agatcgaaag 10620
gcattgccta agccagattt attcaattac tcagaacata attcttatgt tgcaccgcgt 10680
aatgaagtag aggaaaaatt ggtgcagata tggtctaaca ttttacattt acctaaagta 10740
ggcgttactg aaaacttttt cgcgatcggt ggtaatagtt tgaaggcgtt acacttaatt 10800
agtcagattg aggaattatt cgcaaaggag attagtttgg cgacgttgtt gacaaatcca 10860
gttattgcgg acttagctaa agttattcaa gcgaataacc aaatccacaa ttcaccatta 10920
gtgccgatcc aaccgcaggg caagcagcaa ccttttttct gtatccatcc ggcgggtgga 10980
catgtattat gttacttcaa gttggcgcaa tacataggaa cggaccaacc attttacggc 11040
ttgcaggctc aaggttttta cggagatgaa gcgccattga cacgtgttga ggatatggca 11100
tctttgtacg tgaaaacgat acgagagttc caacctcaag gcccgtaccg agtcggtggc 11160
tggtctttcg gcggcgtagt ggcgtacgag gtcgcgcaac aattgcatcg acaaggacaa 11220
gaggtctcat tgttagcaat tttagatagt tatgtgccaa tcttattgga taaacaaaag 11280
ccaatcgatg atgtgtactt ggtgggagtc ttgtctcgtg tcttcggtgg aatgttcggt 11340
caagacaatt tagtaacacc tgaagaaatc gaaaatttga cggtagaaga gaaaatcaat 11400
tacatcattg ataaagctag atcagcacgt atttttcctc cgggagtaga acgacagaac 11460
aatcgtcgta ttttggatgt cttagtgggc actttgaaag caacttatag ttacattcga 11520
cagccttatc cgggcaaggt cacagttttc cgtgcgcgtg aaaaacatat aatggcgccg 11580
gacccaactt tggtctgggt tgaattattt tcagttatgg cggcgcagga aataaagatc 11640
atagacgtac cgggcaatca ctactctttt gtcttagaac cacatgtaca agtattggct 11700
cagagattac aggactgctt agaaaataac tcatgacccg ggtaccgagc tcgaattcag 11760
gcgcgcctat tctaaatgca taataaatac tgataacatc ttatattttg tattatattt 11820
tgtattatcg ttgacatgta taattttgat atcaaaaact gattttccct ctattatttt 11880
cgagatttat tttcttaatt ctctttaaca aactagaaat attgtatata caaaaaatta 11940
taaataatag atgaatagtt taattatagg tgttcatcaa tcgaaaaagc aacgtatctt 12000
atttaaagtg cgttgctttt ttctcattta taaggttaaa taattctcat atatcaagca 12060
aagtgacagg cg 12072

<210> SEQ ID NO 6
<211> LENGTH: 1534
<212> TYPE: DNA
<213> ORGANISM: Artificial Sequence
<220> FEATURE:
<223> OTHER INFORMATION: sequence per se is derived from human thought

<400> SEQUENCE: 6
cccctgatat ttttgactaa accaaatgct aacccagaaa tacaatcact gtgtctaatg 60
aataatttgt tttataaaca cttttttgtt tacttctcat ttttaattag ttataattaa 120
ctaaataata gagcattaaa tatatttaat aaaacttatt taatgcaaaa ttatgactaa 180
catatctata ataaataaag attagatatc aatatattat cgggcaaatg tatcgagcaa 240
gatgcatcgg atcgatccag gaggtatacc tgattaactt tataaggagg aaaaacatat 300
gagtatcgtt caagcgaaat ttgaagcaaa agaaacgagt ttccatgtgg aaggatatga 360
gaagatcgag tacgatttgg tgtatgttga cggcattttt gagatacaaa attctgcgtt 420
ggcggatgta tatcagggat ttggtagatg cttggcgata gttgatgcga atgtgagtcg 480
tttgtatggt aatcagatcc aggcgtattt ccaatactat ggtattgagt tacgtttgtt 540

```
tcctataacg attacggagc ctgataagac gattcagact ttcgagcgag ttattgacgt    600

ctttgctgac ttcaagttag tcagaaaaga accagtcttg gtagtgggtg gtggattaat    660

cacagacgta gtaggcttcg cgtgcagtac ttacagaaga tcttctaact acatccgaat    720

accgacaacg ttaataggtt tgattgatgc tagtgttgct atcaaggtgg cagtaaatca    780

cagaaaatta aagaaccgat tgggagctta ccacgcatca cgaaaagtct tcttagactt    840

ttctttgtta cgaacattgc cgactgatca agtcagaaac ggaatggctg aattagtaaa    900

gatcgcggtc gtggcacatc aggaggtgtt cgagttgtta gagaagtacg gagaagagtt    960

attacgaacg catttcggta atatagacgc tactcctgaa attaaggaga tcgcgcaccg   1020

attgacatac aaagctattc ataagatgtt agagttggag gttcctaact tacacgagtt   1080

ggacttagac cgtgtaatag cttatggtca tacgtggagt ccgacattag aattggctcc   1140

tcgtttgcct atgttccacg gacacgcggt caacgtcgat atggcattca gtgcgacgat   1200

tgctgcacga cgaggttaca ttacgattgc tgagcgtgat agaatcttag gattaatgag   1260

tcgagtcggt ttaagtttgg accaccctat gttggatatt gacatcttat ggcgaggtac   1320

agaatctatc actttaactc gagacggatt attgcgtgct gcaatgccga agcctatagg   1380

cgactgtgta ttcgtcaatg atttgactcg agaagaattg gcagcagcgt tagcggacca   1440

caaagaatta tgtacgagtt atccgcgtgg tggtgaaggc gtcgatgtct atccagtata   1500

tcaaaaagag ttaatcggaa gtgtaaagta accc                               1534
```

<210> SEQ ID NO 7
<211> LENGTH: 583
<212> TYPE: DNA
<213> ORGANISM: artificial sequence
<220> FEATURE:
<223> OTHER INFORMATION: sequence per se is derived from human thought

<400> SEQUENCE: 7

```
ccctgattaa ctttataagg aggaaaaaca tatgttatca ggacatattg aaggacaaac     60

tttaaagatg tttgttcata tgacgaaggc taagaaggta ttagaaattg gaatgttcac    120

aggctactct gcgttagcga tggcagaggc gttaccagag gatggtttgt tagtcgcgtg    180

cgaagttgat ccttacgcag cggagatagg tcaaaaggca ttccagcaat caccacacgg    240

cggcaagata cgagttgagt tggacgcagc tttagcgact ttggacaaat tagcagaagc    300

aggagagagt tttgatttgg ttttcataga cgctgacaag aaggaatacg tggcttattt    360

tcataagttg ttgggaagtt cattattagc tccagacggt ttcatatgcg ttgacaacac    420

tttgttgcaa ggagaagtat atttaccggc ggaggagcga tcagtgaatg gtgaggctat    480

cgcacagttc aatcatactg tcgcaattga tccgcgagtc gagcaagtgt tattgccgtt    540

gagagatggt ttaactatta ttcgtcgtat tcagccataa ccc                      583
```

<210> SEQ ID NO 8
<211> LENGTH: 1411
<212> TYPE: DNA
<213> ORGANISM: artificial sequence
<220> FEATURE:
<223> OTHER INFORMATION: sequence per se is derived from human thought

<400> SEQUENCE: 8

```
ccctgattaa ctttataagg aggaaaaaca tatggctcaa tctttaccat tatcttctgc     60

accagcgact ccgtcattgc catcacagac taagattgct gcgatcatcc agaatatctg    120
```

```
tacgttggcg ttgttgttgt tggctttgcc aattaacgct acgatagtgt ttatcagttt    180

gttagtattt cgaccacaga aggtgaaggc tgctaaccca caaacaatat taatctcagg    240

tggaaagatg actaaagcat tgcagttagc acgatctttc catgcagctg gtcatagagt    300

tgttttggtg gaaacgcata agtattggtt gactggtcac agattctcac aggcagtaga    360

caaattttat actgtccctg caccgcaaga caatccgcaa gcgtatattc aagctttggt    420

agacattgtc aaacaggaaa atatagacgt ctatattccg gtgacatctc cggtcggctc    480

atattacgat tcattggcga agccggaatt gtctcactat tgtgaagtgt ttcacttcga    540

tgcagacata acacaaatgt tagacgacaa atttgcttta actcaaaaag cacgatcttt    600

gggcttgtca gtcccgaagt ctttcaaaat aacttctccg gagcaagtaa ttaacttcga    660

cttctcagga gaaactagaa aatacatctt aaaaagtatt ccatacgaca gtgtacgtcg    720

tttagatttg acaaagttac cttgtgctac gccggaagag acagcagctt tcgttagaag    780

tttgccgatc acgccagaga agccgtggat aatgcaggaa tttataccag gcaaggaatt    840

ttgtacacac tcaactgtca gaaacggaga attacgtttg cactgctgtt gtgagtcatc    900

agctttccaa gtcaactatg agaacgtaaa caatccgcag ataacagaat gggtccaaca    960

ttttgtcaaa gagttaaagt tgactggaca aatctctttc gatttcatac aagctgaaga   1020

tggaacagta tacgctattg agtgtaaccc tcgaactcat tcagcgataa ctactttcta   1080

tgaccatccg caagttgcag aagcttactt gtcacaggct ccaacaacgg agacaattca   1140

accattaaca acatctaaac caacttattg gacatatcat gaagtgtgga gattaacggg   1200

tatccgaagt ttcactcagt tgcaacgatg gttgggcaac atttggcgtg gcactgatgc   1260

gatttaccaa ccggacgacc cgttaccttt cttgatggtt catcattggc aaattccgtt   1320

gttattgttg aataatttgc gacgattaaa gggttggaca cgtattgatt tcaacattgg   1380

aaaattggtc gaattaggag gtgactagcc c                                  1411
```

```
<210> SEQ ID NO 9
<211> LENGTH: 2701
<212> TYPE: DNA
<213> ORGANISM: artificial sequence
<220> FEATURE:
<223> OTHER INFORMATION: sequence per se is derived from human thought

<400> SEQUENCE: 9

ccctgattaa ctttataagg aggaaaaaca tatgcagacg attgatttta atatccgaaa     60

gttgttagtg gaatggaacg cgacacatcg tgattacgac ttgtcacagt ctttgcacga    120

attgatagtt gcacaagttg aaagaactcc tgaagctatt gctgttacgt tcgacaagca    180

gcaattaacg tatcaggaat taaatcataa agcgaaccag ttgggacact acttacaaac    240

gttaggtgtc caaccggaga cgttagtcgg tgtctgtttg gaacgtagtt tggagatggt    300

catttgttta ttaggaatat tgaaggcggg cggtgcttat gtccctatcg acccggaata    360

tcctcaggaa cgtatagctt acatgttaga agactctcag gtgaaggttt tgttgactca    420

agaaaaatta ttaaatcaga tcccgcacca tcaggcacaa acaatatgtg ttgatagaga    480

atgggagaaa atctctacac aagcgaatac aaatccgaaa tcaaatatta agacggataa    540

cttggcatac gtcatttaca cttctggtag tacaggaaaa ccaaaaggtg cgatgaacac    600

gcataaaggc atatgtaatc gattattgtg gatgcaagag gcttatcaga tcgatagtac    660

ggacagtatc ttgcaaaaaa cgccgttctc ttttgatgtt tcagtctggg agtttttctg    720

gacattattg acgggagcgc gattggttat cgctaagcca ggaggccaca aagacagtgc    780
```

-continued

```
atatttgata gatttgataa cacaggagca aattacaact ttacactttg tgccgtcaat    840
gttacaagtc ttcttacaga accgtcacgt aagtaagtgt agttctttaa agcgagtcat    900
ttgctcagga gaggcgttat caattgattt acagaataga tttttccaac acttgcagtg    960
tgagttgcac aacttatatg gtccaacaga agctgctatt gacgtaactt tttggcaatg   1020
tagaaaggat tctaatttaa aatctgtccc gataggtaga cctatagcga atacacaaat   1080
atatatcttg gacgctgatt tacagccggt taacataggc gtaacgggag agatttatat   1140
tggaggtgta ggcgtggctc gtggatattt gaataaagag gagttaacta aagaaaaatt   1200
catcatcaat cctttcccaa actctgaatt caaacgtttg tataaaacgg gcgatttagc   1260
gcgttattta ccagacggca acatagaata tttgggcaga acagattatc aagtgaaaat   1320
acgaggctat agaatagaaa taggcgaaat agagaacgtc ttgtctagtc atccacaggt   1380
gagagaagct gtcgtaatag ctagagatga taacgcgcaa gagaaacaga tcatcgctta   1440
catcacatat aatagtatca agccgcaatt ggacaactta cgagacttct tgaaggcacg   1500
tttgccggat tttatgattc ctgcagcttt tgtgatgttg gaacacttac cgttgactcc   1560
aagtggcaaa gtagatcgaa aggcattgcc taagccagat ttattcaatt actcagaaca   1620
taattcttat gttgcaccgc gtaatgaagt agaggaaaaa ttggtgcaga tatggtctaa   1680
cattttacat ttacctaaag taggcgttac tgaaaacttt ttcgcgatcg gtggtaatag   1740
tttgaaggcg ttacacttaa ttagtcagat tgaggaatta ttcgcaaagg agattagttt   1800
ggcgacgttg ttgacaaatc cagttattgc ggacttagct aaagttattc aagcgaataa   1860
ccaaatccac aattcaccat tagtgccgat ccaaccgcag ggcaagcagc aacctttttt   1920
ctgtatccat ccggcgggtg gacatgtatt atgttacttc aagttggcgc aatacatagg   1980
aacggaccaa ccattttacg gcttgcaggc tcaaggtttt tacggagatg aagcgccatt   2040
gacacgtgtt gaggatatgg catctttgta cgtgaaaacg atacgagagt tccaacctca   2100
aggcccgtac cgagtcggtg gctggtcttt cggcggcgta gtggcgtacg aggtcgcgca   2160
acaattgcat cgacaaggac aagaggtctc attgttagca attttagata gttatgtgcc   2220
aatcttattg gataaacaaa agccaatcga tgatgtgtac ttggtgggag tcttgtctcg   2280
tgtcttcggt ggaatgttcg gtcaagacaa tttagtaaca cctgaagaaa tcgaaaattt   2340
gacggtagaa gagaaaatca attacatcat tgataaagct agatcagcac gtatttttcc   2400
tccgggagta gaacgacaga acaatcgtcg tattttggat gtcttagtgg gcactttgaa   2460
agcaacttat agttacattc gacagcctta tccgggcaag gtcacagttt tccgtgcgcg   2520
tgaaaaacat ataatggcgc cggacccaac tttggtctgg gttgaattat tttcagttat   2580
ggcggcgcag gaaataaaga tcatagacgt accgggcaat cactactctt ttgtcttaga   2640
accacatgta caagtattgg ctcagagatt acaggactgc ttagaaaata actcatgacc   2700
c                                                                   2701
```

EXPRESSION AND SECRETION OF UV ABSORBENT MATERIAL FROM TRANSFORMED BACTERIA

CROSS REFERENCE TO RELATED APPLICATIONS

This application claims priority to U.S. Provisional Application Ser. No. 63/150,137, filed Feb. 17, 2021, which application is hereby incorporated by reference in its entirety.

TECHNICAL FIELD

The present invention relates to a genetically modified bacteria that produces a material with UV absorbing properties.

BACKGROUND OF THE INVENTION

Environmental stressors on humans and the pressures caused by them are increasing in an ever-changing climate. Stressors such as ultraviolet radiation, heat, osmotic pressure, and desiccation can have several effects on the human body including causing skin cancers, oxidative damage and photoaging. Skin cancers are particularly of acute concern. Among skin cancers, melanoma is a cancer of melanocytes and is expected to affect almost 100,000 people in the year 2019. An aggressive malignancy that tends to metastasize, melanoma is responsible for a majority of skin cancer related deaths in spite of representing 5% of cutaneous malignancies. Therefore, more efficient and effective strategies to minimize UV related damage to skin is required that affords passive protection.

The sun protection and sunless tanners market is a $1.4 billion industry with 3 out of 4 adults using sunscreen, tanning products or sunless tanners. However, the effectiveness of synthetic sunscreens depends on applying generous amounts, inadequate coverage, more frequent applications as much as reapplying every one to two hours, ensuring proper storage since their potency can be destroyed if stored at higher than normal temperature conditions, and other factors that are difficult to control. In addition, consumers are getting increasingly conscious about the safety of sunscreen ingredients as well as the impact of these ingredients on the environment. Recent research has revealed that some synthetic sunscreen components can accumulate in aquatic environments and potentially cause harm by acting as hormone disruptors.

As per the FDA, only two sunscreens (zinc oxide and titanium dioxide) have sufficient safety data. In fact, the FDA in February 2019 said that there is insufficient data on 12 of the 16 approved sunscreen molecules to include them in the "generally recognized as safe and effective" (GRASE) category. Additionally, the FDA has also recommended against the use of aminobenzoic acid (PABA) and trolamine salicylate and have placed them in the non-GRASE category. Only zinc oxide and titanium dioxide were able to get a GRASE designation with FDA suggesting insufficient data for other molecules to make a GRASE determination. The FDA also cited the high systemic availability (including significant concentrations in urine, blood plasma, amniotic fluid, and breast milk) along with insufficient absorption and carcinogenicity data of oxybenzone as a concern against a positive GRASE designation. The FDA is also concerned about potential hormonal disruption with the present set of sunscreen molecules, particularly associated with long-term use.

Certain sunscreen molecules such as oxybenzone, octinoxate, etc. have been found to be toxic to coral reefs, sea urchins, and other marine organisms. As per the National Ocean Service, even GRASE sunscreens such as nano-titanium and zinc oxides can harm marine life. Popular beach destinations such as Palau and Hawaii have already imposed bans on several reef-toxic sunscreens. Therefore, a need still exists for a new method of protecting the skin from UV that is environmentally friendly.

SUMMARY OF THE INVENTION

The present invention addresses this need by providing a probiotic technology involving engineered commensal bacteria which, when applied to the skin surface, act as living biofactories of sunscreen molecules. These engineered bacteria produce mycosporine-like amino acids (MAAs) which are natural photoprotective molecules produced by marine cyanobacteria. The MAAs produced by commensal skin bacteria multiply on the skin surface and provide sun protection in a sustained manner. Therefore, the problem is solved in an eco-friendly manner since MAAs are sourced from marine life itself.

In one embodiment, the present invention involves a genetically modified strain of commensal bacteria *Staphylococcus epidermidis* which produces a material with UV absorbing properties. In another embodiment, the material with UV absorbing properties is a mycosporine-like amino acid. In one embodiment, the mycosporine-like amino acid is shinorine. In another embodiment, the bacteria includes the nucleotide sequences shown in SEQ ID NO:6, SEQ ID NO:7, SEQ ID NO:8, and SEQ ID NO:9. In one embodiment, bacteria includes the nucleotide sequence shown in SEQ ID NO:5. In another embodiment, the invention is a topical composition where the bacteria is present in the composition at a concentration of at least 0.1% by weight of the total composition. In one embodiment, the present invention involves a composition including the genetically modified strain of commensal bacteria and a sunscreen.

Another embodiment of the present invention involves a genetically modified strain of bacteria *Escherichia coli* Nissle 1917 which produces a material with UV absorbing properties. In one embodiment, the material with UV absorbing properties is a mycosporine-like amino acid. In another embodiment, the mycosporine-like amino acid is shinorine. In one embodiment, the bacteria includes the nucleotide sequences shown in SEQ ID NO:1, SEQ ID NO:2, SEQ ID NO:3, and SEQ ID NO:4.

One embodiment of the present invention involves a genetically modified strain of commensal bacteria which produces a material with UV absorbing properties, where the bacteria includes a lysis circuit. In another embodiment, the bacteria undergoes lysis in the presence of increased bacterial density and the absence of UV light.

BRIEF DESCRIPTION OF THE DRAWINGS

The foregoing summary, as well as the following detailed description of preferred embodiments of the application, will be better understood when read in conjunction with the appended drawings.

DETAILED DESCRIPTION OF THE INVENTION

Figure 1:
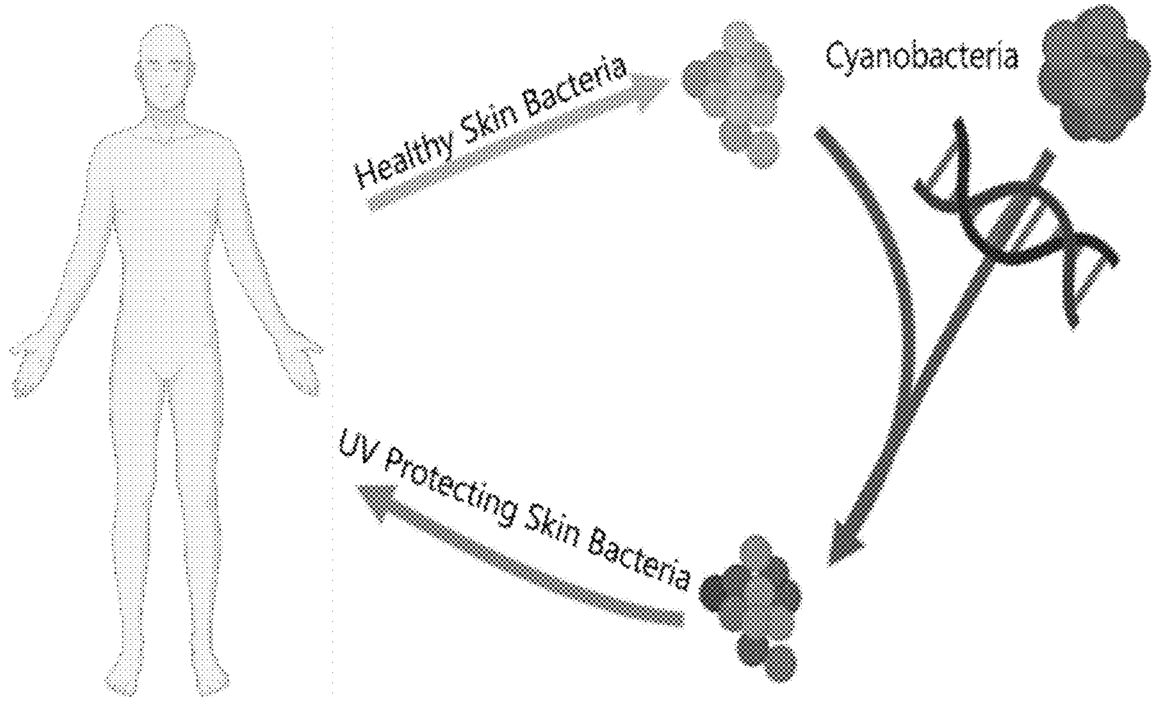
FIG. 1 is a schematic of human skin microbiome transformation into "living factories" on skin secreting natural sunscreens for the protection against environmental stressors.

The details of one or more embodiments of the disclosed subject matter are set forth in this document. Modifications to embodiments described in this document, and other embodiments, will be evident to those of ordinary skill in the art after a study of the information provided herein.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The term "commensal bacteria" as used herein means a bacteria that lives on or in another organism without causing harm.

While the following terms are believed to be well understood by one of ordinary skill in the art, definitions are set forth to facilitate explanation of the disclosed subject matter. Unless defined otherwise, all technical and scientific terms used herein have the same meaning as commonly understood by one of ordinary skill in the art to which the disclosed subject matter belongs.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Application of sunscreens is crucial to mitigate the risk of skin cancers caused as a result of UV radiation-mediated DNA damage. Studies have shown that a majority of the population does not apply sunscreens correctly and in enough quantity to offer the necessary protection. Therefore, most marketed sunscreens end up offering only about 40% of the promised sun protection factor (SPF) due to improper application. These factors leave users more exposed to solar radiation, significantly limiting the sun shielding offered by these products. Additionally, conventional sunscreens presently available in the market are in the form of lotions, creams, or aerosol sprays that need to be frequently reapplied (usually every two to three hours) which further reduces their compliance and increases risks. The present invention introduces a probiotic sunscreen platform which will form an invisible layer of sun protection on the skin surface.

The human skin is the largest organ in the human body and acts as the interface between the insides of the body and the external environment. The exposed part of the skin is composed of entirely dead elements, including epidermis and hair. Incidentally, the only living element on the surface of the skin is the microbiome. The microbiome has an inherent ability to replenish itself, with some bacteria having doubling times as short as 20 minutes. Recent advancements in genetic engineering and synthetic biology have transformed the field and it's now possible to introduce a diverse array of genetically encoded proteins, drugs, enzymes etc into bacteria as plug-and-play systems. The skin microbiome is a vast and underexplored component of the healthy human body and its importance is gradually being appreciated by researchers and dermatologists worldwide.

By genetically engineering bacteria found in healthy human skin, the present invention presents an unprecedented probiotic sunscreen technology that has not been available before. In addition to being novel, the developed technology is the first of its kind to offer sunscreen protection commensurate with the exposure to dermal exposure to sunlight. The developed platform has the potential to be used for numerous parallel dermatological applications.

MAAs

Mycosporine-like amino acids (MAAs) are natural ultraviolet radiation absorbing metabolites produced by marine microorganisms such as cyanobacteria and other algae. One of the most popular MAAs is Shinorine, which has been used as a constituent of sunscreen formulations in the European Union such as "Helionori" and "Helioguard 365." MAAs are photoprotective and are commonly referred to as "microbial sunscreen." They have potent Ultraviolet-A (UV-A) and UV-B absorbing properties along with anti-oxidant characteristics. Additionally, certain MAAs such as mycosporine-glycine and mycosporine-taurine possess significant singlet oxygen scavenging property. They also perform other protective functions in their parent organisms such as protecting against oxidative stress, desiccation, and osmotic stress. UV irradiation promotes the production of MAAs in cyanobacteria. MAAs such as shinorine have also been found to protect against abiotic stress factors such as salinity, dessication, and heat. However, the yield of shinorine, which comes from red algae gathered from the sea, can vary seasonally and geographically, limiting supply.

*S. epidermidis*

The present invention involves the creation of genetically engineered bacteria, commonly found on the human skin, for production of these molecules. The human skin is home to several species of commensal or non-pathogenic bacteria and among them is *Staphylococcus epidermidis*. Interestingly, *S. epidermidis* possesses genes and precursors involved in the biosynthesis of shinorine, and therefore can be a suitable host for production of shinorine through genetic engineering. These genetically engineered strains of *S. epidermidis* can be applied on the skin surface to provide both short term as well as long term protection as these bacteria would as living factories on the skin surface constantly generating shinorine on-demand.

The present invention hijacks the gene cluster from cyanobacteria and engineers *S. epidermidis* to synthesize MAAs in a regulated manner (FIG. 1). The developed genetically engineered strains of *S. epidermidis* can be applied on the skin surface to provide both short term as well as long term protection, as these bacteria serve as "living factories" on the skin surface constantly generating Shinorine on-demand.

While *S. epidermidis* was evaluated as the bacterial template for the "living factory" design, other skin commensal microbiota that might also be effective were screened and identified. For example, commensal bacteria belonging to families, such as *Acinetobacter* (Moraxellaceae) spp., Bacteroidetes and Proteobacteria spp. are also found abundantly and on specific areas of the skin, thus affording the ability to customize this technology to adapt to heterogeneous body and skin constitutions.

There are several optogenetic response elements (ranging from UV-B to far red) to activate the promoters associated with Shinorine. Bacterial promoters such as recA, lexA, etc. which are part of the robust bacterial SOS response upregulate gene transcription upon detection of DNA damage (e.g., by UV light). Understanding these response elements allows us to respond to UV-B or visible light, given that sunlight is composed of both, to activate and regulate production of Shinorine in a time and intensity sensitive fashion.

Figure 2:
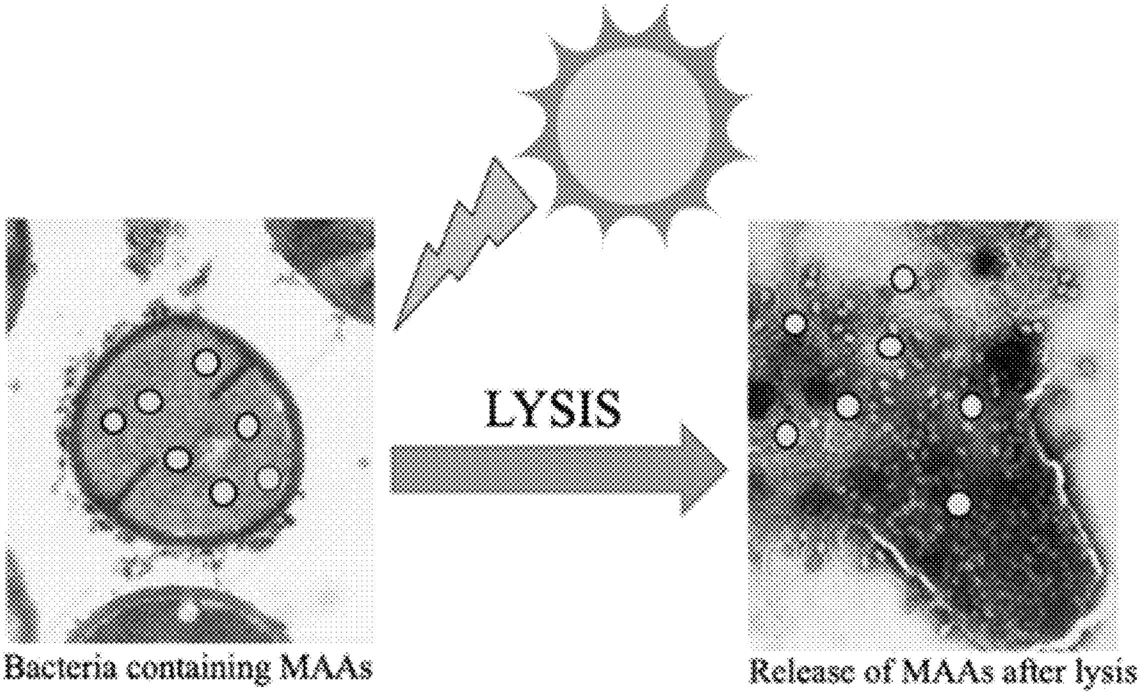
FIG. 2 is a schematic showing release of MAAs from bacteria after UV-induced lysis.

To regulate the bacterial population and potentially release Shinorine extracellularly in significant quantities, in some embodiments, the bacteria is programmed with a lysis circuit to undergo quorum sensing based lysis when high concentrations are reached due to increased bacterial density as well as in the absence of UV light (FIG. 2). With this system, bacterial lysis can be observed in the dark, yet viability is preserved in the presence of UV light and release of sunscreen compounds is commensurate with UV exposure.

Other useful MAAs, such as Gadusol and Palythine also extracted from cyanobacteria, can be incorporated in the bacteria to assess if there is an additive or synergistic UV protective effect along with Shinorine.

Engineering *S. epidermidis* to Synthesize Sunscreen Molecules

The genes responsible for the synthesis of MAA have been identified in cyanobacteria. The present invention introduces a codon-optimized version of these genes in cis in the nonessential attB locus to confer symbiotic *S. epidermidis* the ability to produce sufficient quantities of MAAs. Successful chromosomal integration of the genes of interest and biosynthesis of MAAs can be confirmed using the pMAD system, HPLC and LC/MS.

In one embodiment, a method for in vitro safety and efficacy studies is disclosed. A 3D skin model using primary keratinocytes obtained from human foreskin is inoculated with the engineered bacteria and exposed to UV light. The treatment samples are: (i) control *S. epidermidis*, (ii) recombinant *S. epidermidis* containing Shinorine gene cluster, (iii) MAAs isolated from engineered *S. epidermidis*, (iv) MAA extract obtained from marine sources (Helioguard 365), (v) marketed sunscreen molecule viz. octocrylene. The skin samples are exposed to UV radiation at various doses viz. 7, 14, 21, or 35 mJ cm'. Different UV lamps emitting different wavelengths in the UV-A and UV-B regions are used. Protection from UV light is evaluated by measuring apoptosis, skin proliferation, and selected gene expression. Toxicity is evaluated by checking for key inflammatory mediators and DNA damage.

Regulated Release of Sunscreen Molecules from Engineered *S. epidermidis* Using a UV-Sensitive Promoter to Allow Photoresponsive Modulation Bacterial promoters such as recA, lexA, etc., which are part of the robust bacterial SOS response, upregulate gene transcription upon detection of DNA damage (e.g., by UV light). Introducing a relevant UV-sensitive promoter into *S. epidermidis* allows release of sunscreen molecules commensurate with the intensity of exposure of UV radiation. In one embodiment of the present invention, another stable plasmid (in trans) is introduced in the engineered bacteria consisting of an optimized UV-sensitive promoter and a darkness-inducible host cell lysis sequence derived from the bacteriophage phi X174 that is activated in the absence of UV light. With this system, bacterial lysis can be observed in the dark, yet viability preserved in the presence of UV light and release of sunscreen compounds commensurate with UV exposure. Using HPLC & LC/MS, the amount of MAAs produced can be correlated with the amount of inoculum required and extent of UV exposure. Once both the plasmids responsible for the (i) synthesis of the sunscreen molecule, recA-MAA, and (ii) for the UV radiation-mediated lysis, recA-ϕXI74E, are inserted into the bacteria, the aforementioned safety and efficacy studies may be performed again to establish the safety and efficacy of the final construct.

Figure 3:
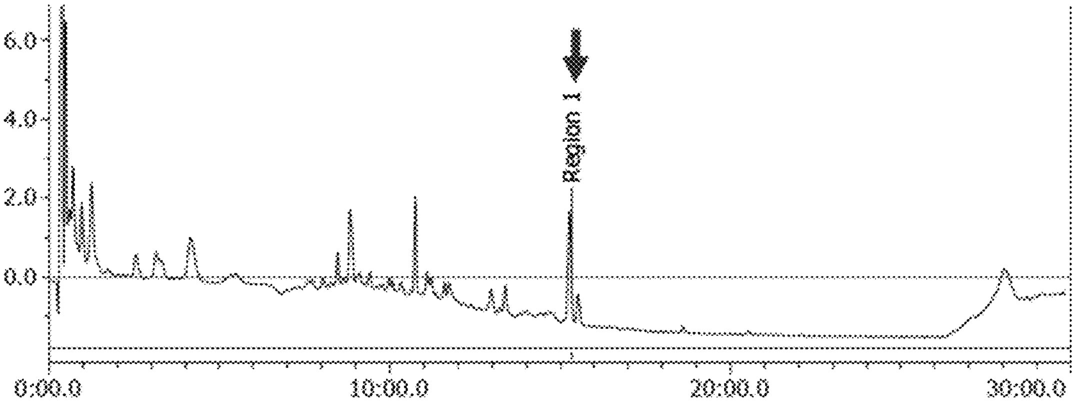
FIG. 3 is a HPLC chromatogram at 333 nm showing Shinorine peak (red arrow) eluting at 15 min timepoint.
Figure 4A:
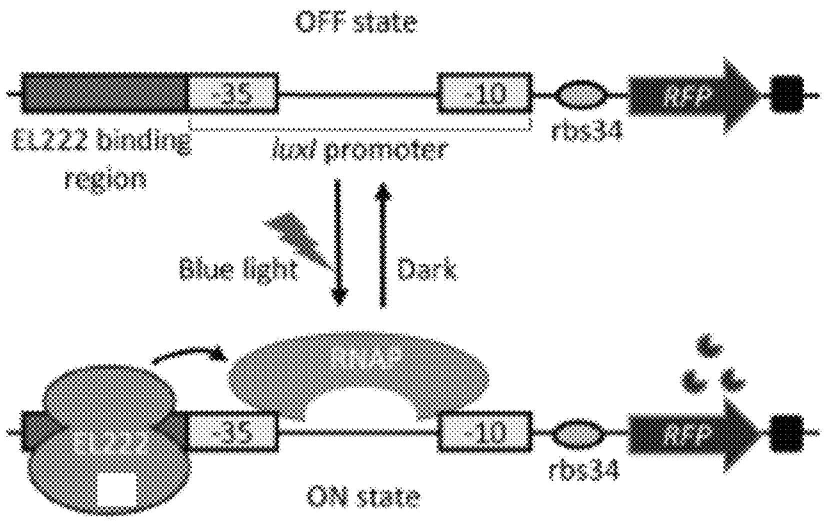
FIGS. 4A-D are series of illustrations showing blue light-mediated transcriptional activation and repression of gene expression in bacteria.
Figure 4B:
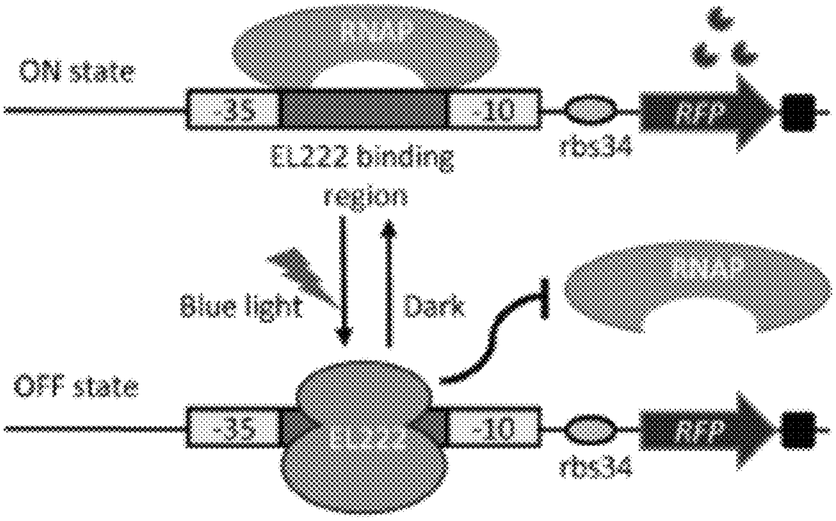
Figure 4C:
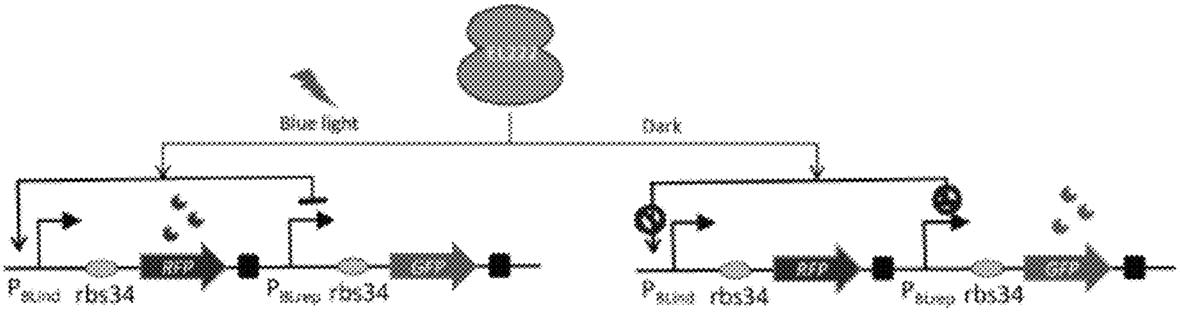
Figure 4D:
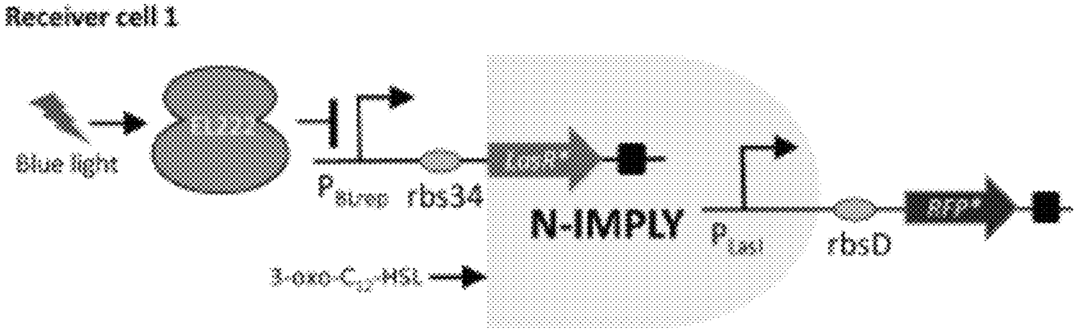

Referring the FIG. 3, HPLC analysis indicates production and release of Shinorine in the bacterial supernatant indicating the successful engineering of *S. epidermidis* to synthesize Shinorine. A number of optogenetic response elements (ranging from UV-B to far red) are utilized to activate the promoters associated with Shinorine. This allows for a response to UV-B or visible light to activate the production. In this embodiment, optogenetic sensors are used involving single protein systems or combinatorial systems involving PhyB-Pif, CryB-CIB, Cry2, LITEs, LACE, LITEZ, TULIP, EL222, TAEL, LANS, BLITZ, and or UVR8-COP1.

FIGS. 4A-4D are a series of illustrations showing blue light-mediated transcriptional activation and repression of gene expression in bacteria. The illustrations show blue-light inducible EL222 protein from *Erythrobacter litoralis*. The luxR box is replaced with the EL222 box, which results in specific activation. This specifically describes the Light-Oxygen-Voltage domain and may be an important part of light activated promoters. This demonstrates a novel bidirectional promoter system for *Escherichia coli* that can be induced or repressed rapidly and reversibly using the blue light dependent DNA-binding protein EL222.

Table 1 shows a list of optogenetic tools for controlling protein-protein interactions and protein oligomerization.

TABLE 1

| Optogenetic Interaction System, Chromophore and Color of Activation | Advantages (+) and Disadvantages (−) of the Tools |
|---|---|
| Phytochrome | |
| −PhyB-PIF3/PIF8<br>Bilin chromophore<br>Activation by red light (660 nm), far-red inactivation (130 nm) | +bimodal switchable<br>+deep tissue penetration of red/far-red light<br>+color tuning possible using different bilin variants<br>−chromophore not ubiquitously available |
| LOV domain | |
| FKF1 and GIGANTEA<br>−AsLOV2-peptides<br>−TULIPs<br>−Magnets<br>FMN chromophore<br>Activation by blue light (470 nm) | +ubiquitous chromophore availability<br>+tuned variants with different time constants and affinities<br>+high dynamic range of improved variants<br>+small size of LOV domain<br>−no color tuning |
| Cryptochrome | |
| −Cry2 and CIB(N)<br>FAD chromophore<br>Activation by blue light (470 nm) | +ubiquitous chromophore availability<br>+tuned variants with different time constants and affinities<br>+high dynamic range of improved variants<br>−large protein size<br>−no color tuning |
| UVR8 | |
| −homodimerization or heterodimerization with Cop1<br>Intrinsic tryptophan cluster as chromophore<br>Activation by UV-B (280 nm) | +no additional chromophore<br>+selective activation when combined with phytochromes<br>+color-tuned variants absorbing UV-C<br>−UV-light induced photodamage<br>−irreversible<br>+increased homodimerization affinity when using UVR8 tandems |
| Fluorescent proteins | |
| −Dronpa K145N<br>Cys-Trp-Gly as chromophore<br>UV/cyan (variable) | +bimodal switchable<br>+GFP-based: small protein, tunable<br>−UV light for activation<br>−low dynamic range<br>−only homodimerization |

Table 2 lists a general review of optogenetics tools, from the perspective of mammalian cells. The tools that are microbially sourced are particularly useful for the present invention.

TABLE 2

| Light | Chromo-phore | System | Tool type | Photo sensor | Co-factor | TF | Activation wavelength | Intensity (μmol $m^{-2}$ $s^{-1}$)* | Model |
|---|---|---|---|---|---|---|---|---|---|
| RED | PCB | PhyB-Pif | Two-hybrid | PhyB | Pif3 | Gal4 DBD-Gal4 AD | 660 nm/750 nm | 1 or 40 | Yeast |
| | | | Two-hybrid | PhyB | Pif6 | TetR DBD-VP16 AD | 660 nm/740 nm | 8/80 | CHO-K1 cells Chicken embryos |
| | | | Two-hybrid | PhyB | Pif6 | TetR DBD-VP16 AD | 660 nm/740 nm | 20/20 | NIH/3T3 cells Zebrafish |
| BLUE | FDA | CRY2-CIB | Two-hybrid | Cry2 | CIB1 | Gal4 DBD-Gal4 AD | 488 nm | 25 μW, 1.7 mW, 4.5 mW | HEK293 cells |
| | | | Two-hybrid | Cry2 | CIB1 | LexA DBD-AD Gal4 | 474 nm | 2.5 mW $cm^{-2}$ | S2 cells Drosophila |
| | | | Heterodimer | Cry2 | CIB1 | $NA^{-}$ | Blue | 42-120 mmol $m^{-2}$ $s^{-1}$ | Zebrafish |
| | | CRY2 | NA | | NA | Gal4 DB (1-65) - VP16AD | 461 nm | 7.4 mW $cm^{-2}$ | HEK293 cells |
| | | LITEs | Heterodimer | Cry2 | CIB1 | TALE-VP64 AD | 473 nm | 5 mW | Neuro2A cells |
| | | LACE | Heterodimer | Cry2 | CIBN | VP64 AD - dCas9 | 450 nm | 48 lumens | HEK293 cells |
| | FMN | LightOn | Homodimer | VVD | $NA^{+}$ | Gal4 (1-65 aa) | 460 nm | 0.84 $Wm^{-2}$<br>90 mW $cm^{-2}$ | HEK293 cells<br>Mice |

TABLE 2-continued

| Light | Chromophore | System | Tool type | Photo sensor | Co-factor | TF | Activation wavelength | Intensity ($\mu$mol $m^{-2}$ $s^{-1}$)* | Model |
|---|---|---|---|---|---|---|---|---|---|
| | | LITEZ | Two-hybrid | GI | FKF1 | ZFP DBD-VP16 AD | 450 nm | 48 lumens | HEK 293T, NIH 3T3, HeLa cells |
| | | TULIP | Two-hybrid | LOV-pep | ePDZ | Gal4 DBD-Gal4 AD | 461 nm | 5.8 mW $cm^{-2}$ | Yeast |
| | | EL222 | Dimer | LOV | NA | HTH DBD-VP16 AD | 465 nm | 8 mW $cm^{-2}$ | HEK293 cells Zebrafish |
| | | TAEL | Dimer | LOV | NA | HTH DBD-KalTA4 AD | 488 nm | 1.6 mW $cm^{-2}$ | HEK293 cells |
| | | LANS | NLS shuttle | asLOV2 | NA | LexA DBD-Gal4 AD | 455 nm | 6 mW $cm^{-2}$ | Yeast |
| | | LINuS | NLS shuttle | asLOV2 | NA | LexA DBD-VP64 AD | 460 nm | 10 | Yeast HEK293 cells |
| | | LINX | NES shuttle | asLOV2 | NA | LexA DBD-Gal4 AD | 488 nm | 8 μS/pixel | HEK293 cells |
| | | LEXY | NES shuttle | asLOV2 | NA | LexA DBD-VP16 AD | 490 nm | Not specified | H1299 cells |
| | | BLITZ | Dimer | Ciy2/asLOV2 | CIBN/NA | TetR-VP16 AD | 473 nm | 1.7 mW | HEK293 cells |
| UV-B | NA | UVR8-COP1 | Two-hybrid | UVR8 | COP1 | Gal4 DBD-NF-κB AD | 280-375 nm 290-310 nm | 25 J $m^{-2}$ 0.7 mW | U2OS cells |

*Unless specified in other light units;
NA, not applicable;
NA– light negatively regulate gene expression.

The present invention also encompasses other skin commensal microbiota. Table 3 shows the top 10 abundant bacteria per Byrd et al. Apart from this, other families such as *Acinetobacter* spp., Bacteroidetes and Proteobacteria can be used.

TABLE 3

| Bacteria | | | |
|---|---|---|---|
| Dry | Moist | Sebaceous | Foot |
| *Propionibacterium acnes* | *Corynebacterium tuberculostearicum* | *Propionibacterium acnes* | *Corynebacterium tuberculostearicum* |
| *Corynebacterium tuberculostearicum* | *Staphylococcus hominis* | *Staphylococcus epidermidis* | *Staphylococcus hominis* |
| *Streptococcus mitis* | *Propionibacterium acnes* | *Corynebacterium tuberculostearicum* | *Staphylococcus warneri* |
| *Streptococcus oralis* | *Staphylococcus epidermidis* | *Staphylococcus capitis* | *Staphylococcus epidermidis* |
| *Streptococcus pseudopneumoniae* | *Staphylococcus capitis* | *Corynebacterium simulans* | *Staphylococcus capitis* |
| *Streptococcus sanguinis* | *Corynebacterium fastidiosum* | *Streptococcus mitis* | *Staphylococcus haemolyticus* |
| *Micrococcus luteus* (Gram negative) | *Corynebacterium afermentans* | *Staphylococcus hominis* | *Micrococcus luteus* |
| *Staphylococcus epidermidis* | *Micrococcus luteus* | *Corynebacterium aurimucosum* | *Corynebacterium afermentans* |
| *Staphylococcus capitis* | *Enterobacter aerosaccus* | *Corynebacterium kroppenstedtii* | *Corynebacterium simulans* |
| *Veillonella parvula* (Gram negative, anaerobic) | *Corynebacterium simulans* | *Corynebacterium amycolatum* | *Corynebacterium resistens* |

To facilitate secretion/excretion of the MAA to the external environment, bacteria's natural secretion system is modified to bind and secrete the MAAs that are generated within. This enables the MAA to provide sufficient protection against UV radiation and other photoaging processes. Table 4 highlights the various gram-positive and gram-negative related secretion systems. The table lists genes and transporters related to amino acid production in *Corynebacterium glutamicum* and *Escherichia coli*: uptake and excretion systems.

TABLE 4

| Transporter | Gene(s) | Substrate(s) | Characteristics |
|---|---|---|---|
| | | *Corynebacterium glutamicum* | |
| AroP | aroP | L-Tyr, L-Phe | Aromatic amino acids uptake system |
| BrnQ | brnQ | L-Be | $Na^+$-coupled uptake system |
| GluABCD | gluABCD | L-Glu | Binding protein-dependent uptake system, expression glucose-repressed |
| Glutamate permease | ? | L-Glu | Uptake active in complex medium |
| LysE | iysE | L-Lys, L-Arg | Exporter, expression regulated by LysG, coinducers L-citrulline and L-histidine |
| Lysl | iysi | L-LyS, L-Ala, L-Val, L-Lev | Low capacity antiporter |
| ThrE | thrE | L-Tlu$^-$, L-Ser | Export carrier |
| | | *Escherichia coli* | |
| AroP | aroP | L-Trp, L-Tyr, L-Phe | General uptake system for aromatic amino acids |
| Aspartate/glutamate carrier | ? | L-Asp, L-Glu | Binding protein-dependent uptake system, inhibited by cysteate |
| GltP | gitP | L-Asp, L-Glu | $Na^-$F-independent uptake, inhibited by cysteate and 5 hydroxyaspartate |
| GltS | gitS | L-Glu | $Na^-$L dependent uptake, inhibited by a methylglutamate |
| Glutamate excretion carrier | | L-Glu | Stringent response-related export |
| LB/1 | INGETAI | L-Len L-Ile, L-Val, L-Ala, L-Thr. L-Hom | Binding-protein-dependent uptake system, expression repressed by LRP |
| Orf299 | ydeD | L-Cys and components of the cysteine pathway | Major facilitator protein involved in efflux |
| PheP | pheP | L-Phe | High-affinity uptake system specific for phenylalarine |
| RhtA | rhtA | | Confer resistance to high concentrations of homoserine and threonine, putative threonine excretion carriers |
| RhtB | rhtB | | |
| RhtC | rhtC | | |
| SstT | sstT | L-Set, L-Thr | Ne-coupled serine/threonine importer |
| TdcC | tdcC | L-Lea L-Sec. L-Tbr, L-Hom | Importer active under anaerobic conditions |
| Threonine permease | ? | L-Thr, L-Ser | $Na^-$L independent uptake system |

The present invention is a unique sunscreen technology which not only significantly improves consumer compliance by eliminating the need of frequent reapplications for effective protection, but also circumvents detrimental impact on human health and the environment. Since the strategy of this invention is to deliver the source of the natural sunscreens, the engineered bacteria, as "living skin-protective factories", it will significantly reduce the cost of the production, unlike current sunscreens that require production, purification and scale-up under good manufacturing practice (GMP) at a pharmaceutical and industrial scale. This platform has the potential to be customizable to different skin and body types—normal, dry, oily—as bacteria other than *S. epidermidis*, such as those belonging to the Bacteroidetes and Proteobacteria families can be used as templates with unique combinations of promoters and regulatory elements to regulate production, release and activity of synthesized molecules.

In one embodiment, the present invention is a probiotic sunscreen technology that enables continuous and extended release of UV filtering molecules on the skin surface with photo/dark-responsive promoters providing modulated release of these natural sunscreens based on the intensity of UV exposure to mitigate environmental stress.

In another embodiment, the present invention is incorporated in a topical composition (it is applied topically to the skin). In one embodiment, the modified bacteria is present in the topical composition at a concentration of at least 0.1% by weight of the total composition. The topical composition may be in the form of a cream, lotion, emulsion, gel, ointment, liquid or aerosol spray. In another embodiment, the bacteria of the present invention is used in a composition with a traditional sunscreen.

Figure 5:
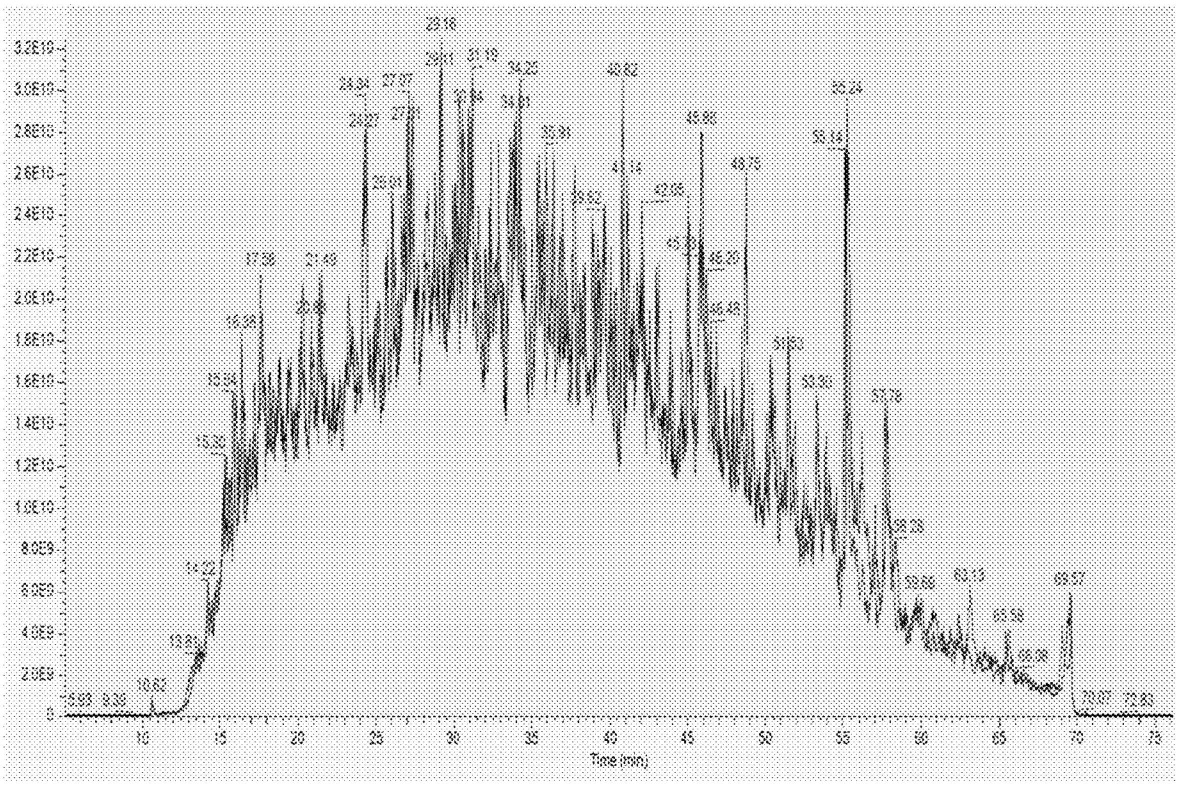
FIG. 5 is a nanoLC-MS/MS chromatogram indicating positive identification of MAA producing enzymes by the engineered bacteria.
Figure 6:
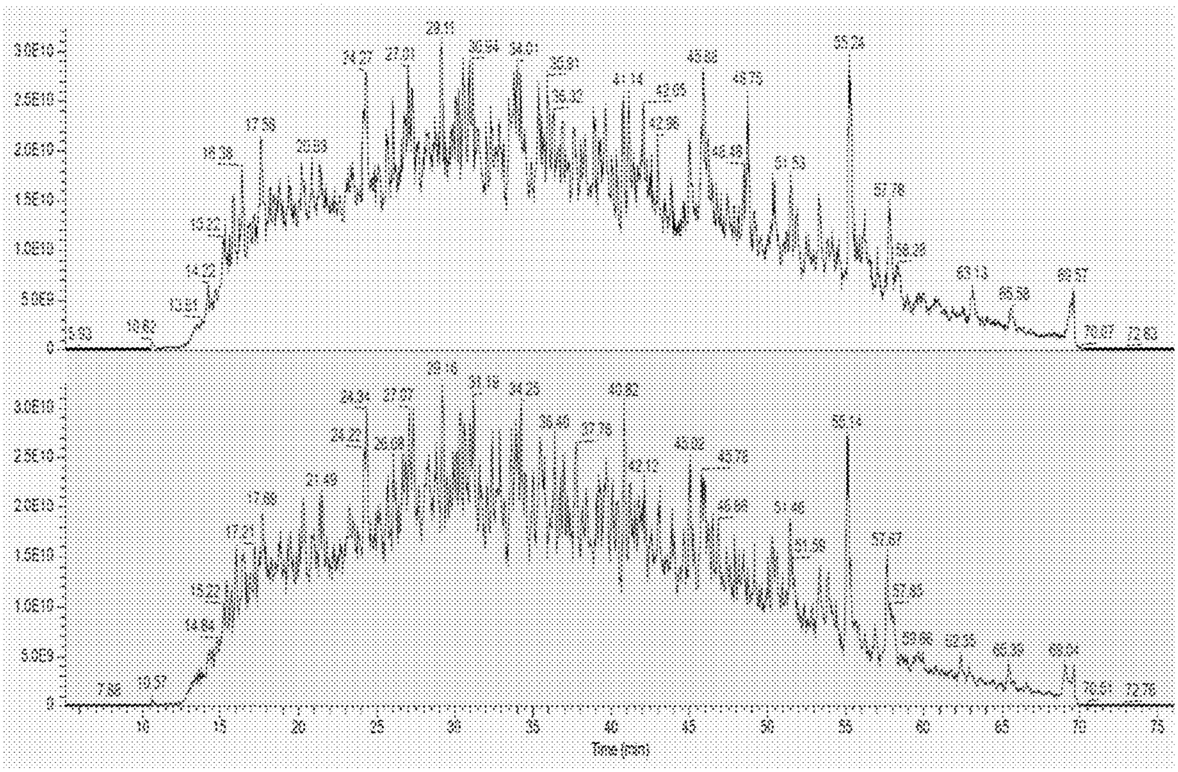
FIG. 6 is a pair of nanoLC-MS/MS chromatograms indicating positive identification of MAA producing enzymes by the engineered bacteria.

The examples (presented below) show the successful engineering of bacteria containing the genes responsible for MAA production. Transformed colonies submitted for Sanger sequencing gave a positive confirmation for MAA genes. NanoLC-MS/MS data indicated presence of enzymes responsible for production of MAAs. There are four enzymes required to synthesize shinorine and LC-MS/MS chromatogram confirmed their presence (see FIGS. 5 and 6).

Figure 7:
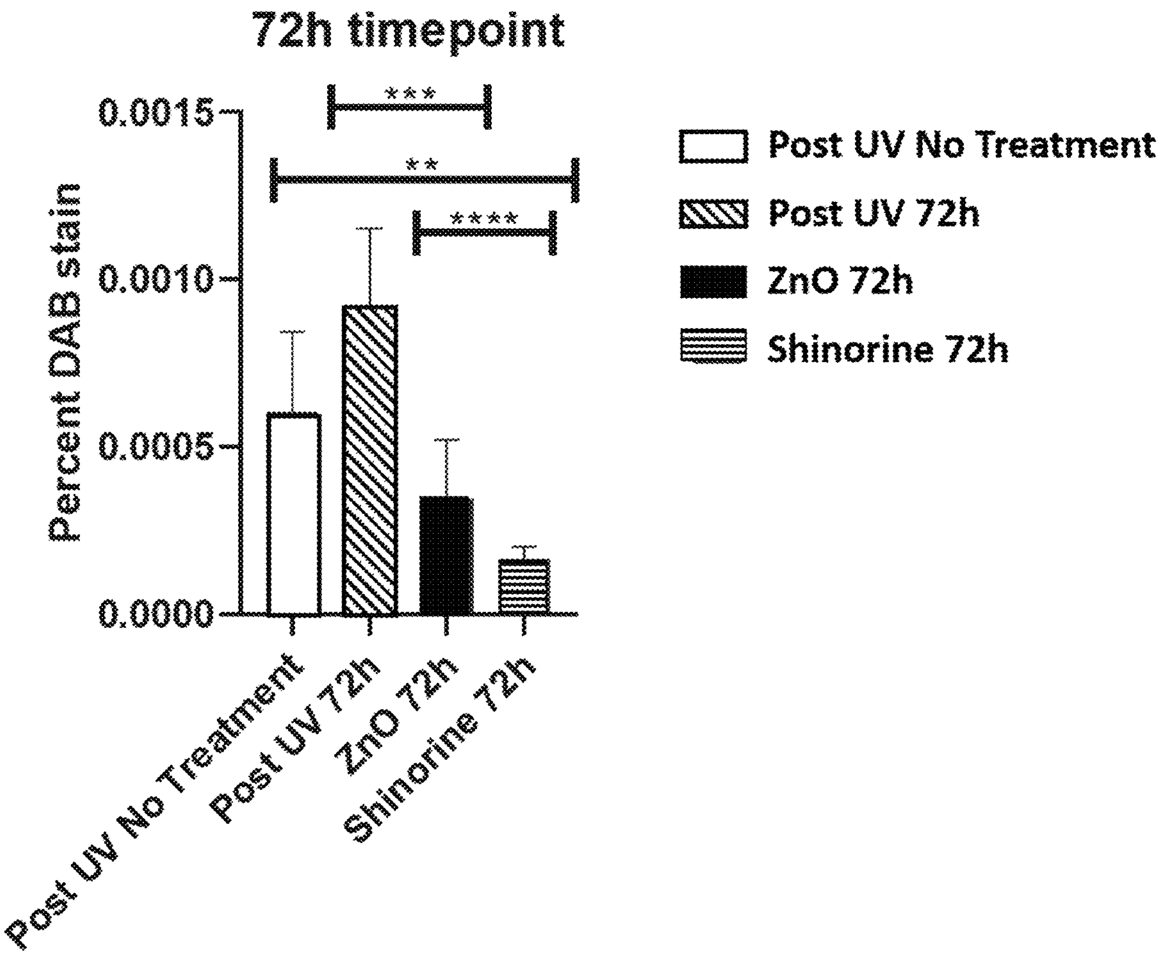
FIG. 7 is a graph showing the significant efficacy of shinorine vs. 10% ZnO 72 h post UV irradiation.
Figure 8:
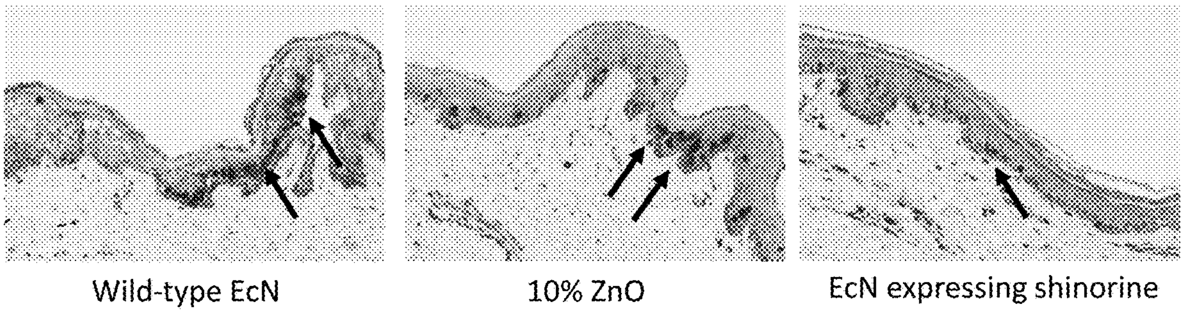
FIG. 8 is a series of images showing cleaved caspase-3 IHC staining of human skin tissues incubated with overnight culture of WT EcN, 10% ZnO, or EcN expressing shinorine 24 h post UV irradiation.
Figure 9:
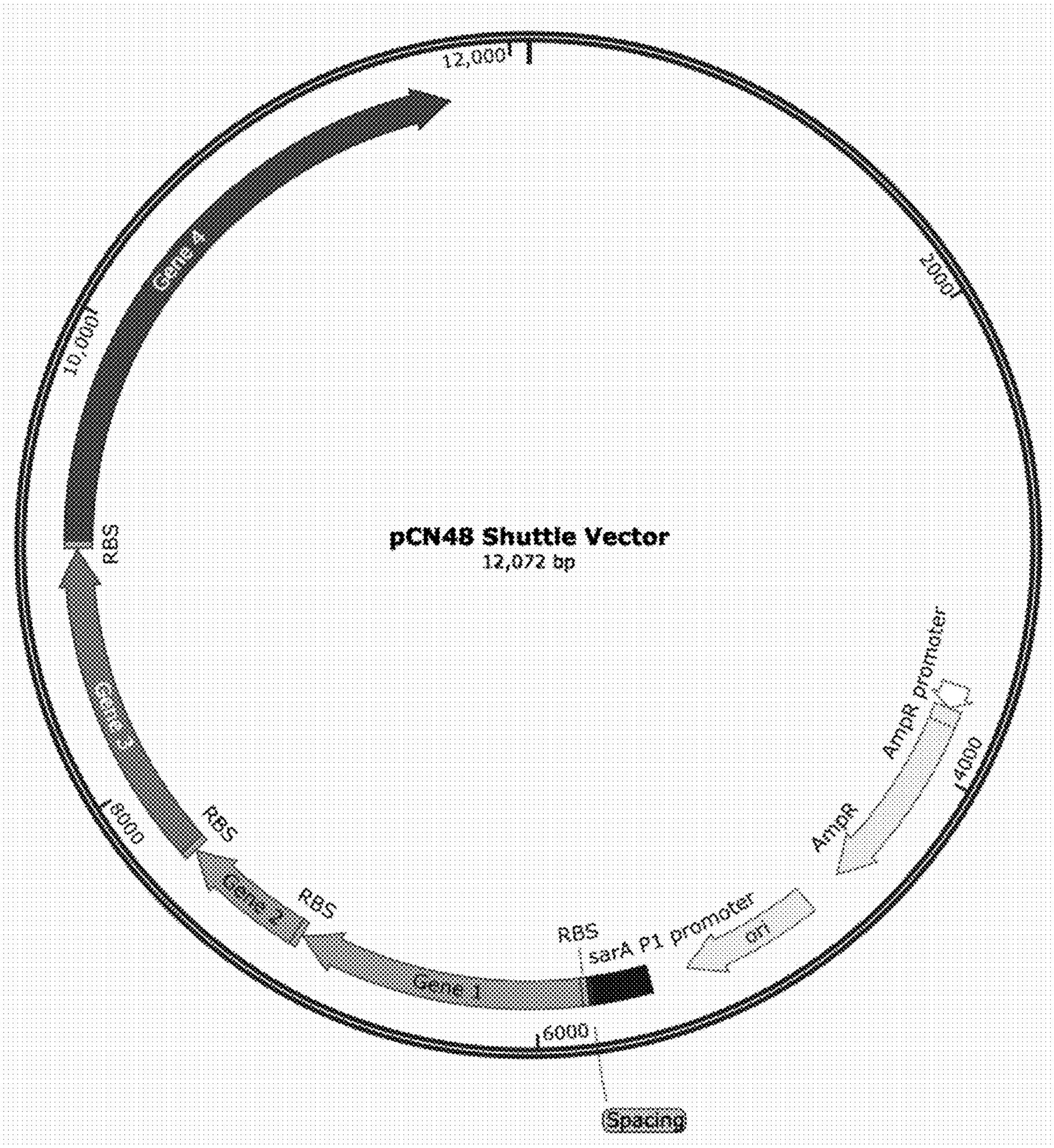
FIG. 9 is a plasmid map of pCN48-Ava3858-3855.

Efficacy studies indicated that shinorine was significantly effective in preventing and/or reducing UV-induced DNA damage compared to untreated group three days post exposure. Furthermore, it was also significantly more effective than a 10% zinc oxide which is a gold standard for sun protection (see FIGS. 7 and 8). This outcome bolsters the photoprotective capacity of shinorine in preventing UV induced skin damage. Evaluating the use of live bacteria on skin tissue also gave encouraging results with IHC images indicating EcN-shinorine's protective effect against UV exposure 24 h post irradiation.

EXAMPLES

Example 1—Engineering MAA-Producing Commensal Bacteria

Several studies were conducted on MAAs and the underlying genes in cyanobacteria responsible for their production. Codon-optimized double stranded DNA fragments were amplified using polymerase chain reaction (PCR) and purified using gel electrophoresis. The dsDNA fragments were designed in such a way as to allow blunt end ligation in the pCN48 plasmid using the Smal site. A restriction digest using Smal enzyme was performed to linearize the plasmid, followed by dephosphorylation using calf intestinal phosphatase (CIP) to prevent the plasmid to close onto itself.

The gene of interest is ligated into the plasmid using T4 DNA ligase. Post ligation, chemically competent DH5a cells are transformed and selected using ampicillin. The plasmids from several transformed colonies are isolated and sent for Sanger Sequencing to check and corroborate successful addition of the gene of interest into the plasmid. Bacterial colonies containing the correct plasmid are isolated and the above process is performed again until all four genes of interest are successfully incorporated. The complete plasmid is initially incorporated into *E. coli* Nissle 1917 (EcN) before being transferred to *S. epidermidis*.

Example 2—Validation of MAA Production by the Engineered Bacteria

1% of overnight cultures were inoculated into 100 ml of fresh LB broth supplemented with the appropriate antibiotic and similarly grown at 37° C. and 200 rpm until OD600 reaches 0.9-1.0 (approx. 3.00-6.00 hr.). Cultures were spun at 4° C. for 15 min, 3500×g, and cells were resuspended in 5-10 volumes of the Bacterial cell lysis buffer (Gold Bio), supplemented with DTT and EDTA (5 mM), and Lysozyme (40 mg/ml), DNase (800 U/ml) and RNase (24 U/ml). Following vortexing, and 5 min incubation on ice, suspensions were incubated at 37° C. for 60 min and lysates were centrifuged at 20,000×g, 4° C. for 30 min, and the clear lysate was collected and quantified using BCA assay (Thermo Scientific).

Protein samples were dried in a speed vac and resuspended in TEAB buffer according to standard in-solution digestion protocol. Samples were reduced with TCEP (tris-(2-carboxyethyl) phosphine) and alkylated with MMTS (methyl-methane-thiosulfonate). Samples were digested overnight at 37° C. and reactions were stopped by adding 10% formic acid. These samples were dried and resuspended in 0.1% formic acid. 5 (~1 μg) of each sample was analyzed by NanoLC-MS/MS (Orbitrap Eclipse) and was searched against a combined database consisting of the *E. coli* Nissle 1917 database accessed from the Biocyc.org website and a database containing the MAA sequences using Proteome discoverer ver 2.4 and the Sequest HT search algorithm using standard LFQ workflow (Thermo scientific).

Example 3—Establishing the In Vitro Efficacy of Engineered Bacteria

MAAs extracted from the engineered bacteria of the present invention were evaluated. Human skin was obtained from discarded tissue from elective procedures. The skin tissue was cleaned, trimmed, sterilized and plated in an organ culture medium overnight at 33° C. MAA extract or appropriate controls were applied on skin tissues, after which they were exposed to 135 mJ/cm2 UV-A and UV-B light. The application of live bacteria on human skin tissue was subsequently tested. Different treatments viz. overnight culture of wild type EcN, 10% zinc oxide solution, or overnight culture of EcN expressing shinorine were applied on human skin explants. Treatments were allowed to equilibrate with skin tissue for 1 hour, after which tissues were exposed to UV radiation. The tissues were then incubated for different durations and subsequently fixed. Cleaved caspase-3 immunohistochemical staining was performed to check for DNA damage. Slides were imaged using Leica Slide Scanner and representative images were captured. The captured images were quantified using ImageJ with a modified, previously published protocol (Crowe and Yue, 2019).

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of"

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

SEQUENCES

```
SEQ ID NO: 1
tgattaactt tataggaggt aaaaacatat gagtatcgtc caagcaaagt ttgaagctaa      60

ggaaacatct tttcatgtag aaggttacga aaagattgag tatgatttgg tgtatgtaga     120

tggtattttt gaaatccaga attctgcact agcagatgta tatcaaggtt ttggacgatg     180

cttggcgatt gtagatgcta acgtcagtcg gttgtatggt aatcaaattc aggcatattt     240

ccagtattat ggtatagaac tgaggctatt tcctattacc attactgaac cagataagac     300

tattcaaact ttcgagagag ttatagatgt ctttgcagat ttcaaattag tccgcaaaga     360

accagtatta gtcgtgggtg gcggtttaat tacagatgtt gtcggctttg cttgttctac     420

atatcgtcgc agcagcaatt acatccgcat tcctactaca ttgattggat taattgatgc     480

cagtgtagca attaaggtag cagttaatca tcgcaaactg aaaaaccgtt tgggtgctta     540

tcatgcttct cgcaaagtat ttttagattt ctccttgttg cgtactctcc ctacagacca     600

agtacgtaac gggatggcgg aattggtaaa aatcgctgta gtagcgcatc aagaagtttt     660

tgaattgttg gagaagtacg gcgaagaatt actacgtact cattttggca atatagatgc     720

aactccagag attaaagaaa tagcccatcg tttgacttac aaagctatcc ataagatgtt     780

ggaattggaa gttcccaacc tgcatgagtt agacctagat agggtgattg cttacggtca     840
```

-continued

| SEQUENCES |
| --- |

```
cacttggagt cccaccttgg aacttgcgcc tcgtctaccc atgttccacg gacacgccgt      900
taatgtagat atggctttct cggcaacgat cgccgcccgt agaggatata ttacaattgc      960
agaacgcgat cgtattttag gattaatgag tcgcgttggt ctatccctcg accatcccat     1020
gttggatata gatattttgt ggcgtggtac tgaatctatc acattaactc gtgatggttt     1080
gttaagagct gctatgccaa aacccattgg tgattgtgtc ttcgtcaatg acctgacaag     1140
agaagaatta gcagccgcat tagctgacca caaagaactt tgtaccagtt atccccgtgg     1200
tggtgaaggt gtggatgtgt atcccgttta tcaaaaagaa ttaatcggga gtgttaaata     1260
a                                                                     1261
```

SEQ ID NO: 2

```
tgattaactt tataaggagg aaaaacatat gctttctggt catatcgaag gacaaacctt       60
aaagatgttt gttcacatga ccaaagctaa aaaagtctta gaaattggga tgtttaccgg      120
ttattcggcg ctggcgatgg cggaagcatt accagaggat ggactgcttg tggcttgtga      180
agttgaccct tacgcggcgg aaattggaca gaaagccttt caacaatctc cccacggtgg      240
aaagattcgt gtggaattgg atgcagcctt agcaactctt gataagttag cagaagctgg      300
ggagtctttt gacttggtat ttatcgacgc agataaaaaa gagtatgtag cctattttca      360
caagttgcta ggtagcagtt tgttagcacc agatggcttt atttgtgtag ataacacctt      420
attacaaggg gaagtttatc taccagcaga ggaacgtagc gtcaatggtg aagcgatcgc      480
gcaatttaat catacagtag ctatagaccc ccgtgtagaa caggttttgt tgccgttgcg      540
agatggttta acaattatcc gcagaataca accttaa                               577
```

SEQ ID NO: 3

```
tgattaactt tataaggagg aaaaacatat ggcacaatcc cttccccttt cttccgcacc       60
tgctacaccg tctcttcctt cccagacgaa aatagccgca attatccaaa atatctgcac      120
tttggctttg ttattactag cattgcccat taatgccacc attgttttta tatccttgtt      180
agtcttccga ccgcaaaagg tcaaagcagc aaacccccaa accattctta tcagtggcgg      240
taagatgacc aaagctttac aactagcaag gtcattccac gcggctggac atagagttgt      300
cttggtggaa acccataaat actggttgac tggtcatcgt ttttcccaag cagtggataa      360
gttttacaca gtccccgcac cccaggacaa tccccaagct tacattcagg ctttggtaga      420
tatcgtcaaa caagaaaaca tcgatgttta tattcccgtc accagtccag tgggtagcta      480
ctacgactca ttagccaaac cagagttatc ccattattgc gaagtgtttc actttgacgc      540
agatattacc caaatgttgg atgataaatt tgcgttgaca caaaaagcgc gatcgcttgg      600
tttatcagta cccaaatcct ttaaaattac ctcaccagaa caagtcatca acttcgattt      660
ttctggagag acacgtaaat acatcctcaa aagcattccc tacgactcag tgcggcggtt      720
ggacttaacc aaactcccct gtgctactcc agaggaaaca gcagcattcg tcagaagttt      780
gccaattact cccgaaaaac cgtggattat gcaggaattt atccccggta aggaattctg      840
cacccatagc accgttcgga atggggaact cagactgcat tgctgttgcg aatcttcagc      900
cttccaagtt aattatgaga atgtaaataa cccgcaaatt accgaatggg tacagcattt      960
tgtcaaggaa ctgaaactga caggacagat ttcctttgac tttatccaag ccgaagacgg     1020
aacagtttac gccatcgagt gtaacccccg cacacattca gcaattacca cattttacga     1080
ccaccccccag gtagcagaag cgtacttgag tcaagcaccg acgactgaaa ccatacaacc     1140
```

-continued

SEQUENCES

```
actaacgaca agcaagccta cctattggac ttatcacgaa gtttggcgtt taactggtat     1200

ccgttctttc acccagttgc aaagatggct ggggaatatt tggcgcggga ctgatgcgat     1260

ttatcagcca gatgacccct taccgttttt gatggtacat cattggcaaa ttcccctact     1320

gttattgaat aatttgcgtc gtcttaaagg ttggacgcgg atagatttca atattgggaa     1380

gttggtggaa ttggggggag attag                                           1405

SEQ ID NO: 4
atgcagacta tagattttaa tattcgtaag ttacttgtag agtggaacgc gacccacaga       60

gattatgatc tttcccagag tttacatgaa ctaattgtag ctcaagtaga acgaacacct      120

gaggcgatcg ctgtcacctt tgacaagcaa caactaactt atcaagaact aaatcataaa      180

gcaaaccagc taggacatta tttacaaaca ttaggagtcc agccagaaac cctggtaggc      240

gtttgtttag aacgttcctt agaaatggtt atctgtcttt taggaatcct caaagctggg      300

ggtgcttatg ttcctattga ccctgaatat cctcaagaac gcatagctta tatgctagaa      360

gattctcagg tgaaggtact actaactcaa gaaaaattac tcaatcaaat tccccaccat      420

caagcacaaa ctatctgtgt agatagggaa tgggagaaaa tttccacaca agctaatacc      480

aatcccaaaa gtaatataaa aacggataat cttgcttatg taatttacac ctctggttcc      540

actggtaaac caaaaggtgc aatgaacacc cacaaaggta tctgtaatcg cttattgtgg      600

atgcaggaag cttatcaaat cgattccaca gatagcattt tacaaaaaac cccctttagt      660

tttgatgttt ccgtttggga gttcttttgg actttattaa ctggcgcacg tttggtaata      720

gccaaaccag gcggacataa agatagtgct tacctcatcg atttaattac tcaagaacaa      780

atcactacgt tgcattttgt cccctcaatg ctgcaagtgt ttttacaaaa tcgccatgta      840

agcaaatgca gctctctaaa aagagttatt tgtagcggtg aagctttatc tatagattta      900

caaaatagat tttccagca tttgcaatgt gaattacata acctctatgg cccgacagaa      960

gcagcaattg atgtcacatt ttggcaatgt agaaaagata gtaatttaaa gagtgtacct     1020

attggtcgtc ccattgctaa tactcaaatt tatattcttg atgccgattt acaaccagta     1080

aatattggtg tcactggtga aatttatatt ggtggtgtag ggttgctcg tggttatttg     1140

aataaagaag aattgaccaa agaaaaattt attattaatc cctttcccaa ttctgagttt     1200

aagcgacttt ataaaacagg tgatttagct cgttatttac ccgatggaaa tattgaatat     1260

cttggtagaa cagattatca agtaaaaatt cggggttata gaattgaaat tggcgagatt     1320

gaaaatgttt tatcttcaca cccacaagtc agagaagctg tagtcatagc gcgggatgat     1380

aacgctcaag aaaaacaaat catcgcttat attacctata actccatcaa acctcagctt     1440

gataatctgc gtgatttcct aaaagcaagg ctacctgatt ttatgattcc agccgctttt     1500

gtgatgctgg agcatcttcc tttaactccc agtggtaaag tagaccgtaa ggcattacct     1560

aagcctgatt tatttaatta tagtgaacat aattcctatg tagcgcctcg gaatgaagtt     1620

gaagaaaaat tagtacaaat ctggtcgaat attctgcatt tacctaaagt aggtgtgaca     1680

gaaaactttt tcgctattgg tggtaattcc ctcaaagctc tacatttaat ttctcaaatt     1740

gaagagttat ttgctaaaga gatatcctta gcaacacttt taacaaatcc agtaattgca     1800

gatttagcca aggttattca agcaaacaac caaatccata attcacccct agttccaatt     1860

caaccacaag gtaagcagca gcctttcttt tgtatacatc ctgctggtgg tcatgtttta     1920

tgctatttta aactcgcaca atatatagga actgaccaac cattttatgg cttacaagct     1980
```

-continued

| SEQUENCES | |
|---|---|
| caaggatttt atggagatga agcacccttg acgcgagttg aagatatggc tagtctctac | 2040 |
| gtcaaaacta ttagagaatt tcaaccccaa gggccttatc gtgtcggggg gtggtcattt | 2100 |
| ggtggagtcg tagcttatga agtagcacag cagttacata gacaaggaca agaagtatct | 2160 |
| ttactagcaa tattagattc ttacgtaccg attctgctgg ataaacaaaa acccattgat | 2220 |
| gacgtttatt tagttggtgt tctctccaga gtttttggcg gtatgtttgg tcaagataat | 2280 |
| ctagtcacac ctgaagaaat agaaaattta actgtagaag aaaaaattaa ttacatcatt | 2340 |
| gataaagcac ggagcgctag aatattcccg cctggtgtag aacgtcaaaa taatcgccgt | 2400 |
| attcttgatg ttttggtggg aactttaaaa gcaacttatt cctatataag acaaccatat | 2460 |
| ccaggaaaag tcactgtatt tcgagccagg gaaaaacata ttatggctcc tgacccgacc | 2520 |
| ttagtttggg tagaattatt ttctgtaatg gcggctcaag aaattaagat tattgatgtc | 2580 |
| cctggaaacc attattcgtt tgttctagaa ccccatgtac aggttttagc acagcgttta | 2640 |
| caagattgtc tggaaaataa ttcatgactc ga | 2672 |
| SEQ ID NO: 5 | |
| cctttgcgaa agagttaata agttaacaga agatgaacca aaactaaatg gtttagcagg | 60 |
| aaacttagat aaaaaaatga atccagaatt atattcagaa caggaacagc aacaagaaca | 120 |
| acaaaagaat caaaaacgag atagaggtat gcacttatag aacatgcatt tatgccgaga | 180 |
| aaacttattg gttggaatgg gctatgtgtt agctaacttg ttagcgagtt ggttggactt | 240 |
| gaattgggat taatcccaag aaagtaccaa ctcaacaaca cataaagccc tgtaggttcc | 300 |
| gaccaataag gaaattggaa taaagcaata aaaggagttg aagaaatgaa attcagagaa | 360 |
| gcctttgaga attttataac aagtaagtat gtacttggtg ttttagtagt tttaactgtt | 420 |
| taccagataa tacaaatgct taaataaaaa aagacttgat ctgattagac caaatctttt | 480 |
| gatagtgtta tattaataac aaaataaaaa ggagtcgctc acgccctacc aaagtttgtg | 540 |
| aacgacatca ttcaaagaaa aaaacactga gttgttttta taatcttgta tatttagata | 600 |
| ttaaacgata tttaaatata catcaagata tatatttggg tgagcgatta cttaaacgaa | 660 |
| attgagatta aggagtcgat tttttatgta taaaaacaat catgcaaatc attcaaatca | 720 |
| tttggaaaat cacgatttag acaatttttc taaaaccggc tactctaata gccggttgga | 780 |
| cgcacatact gtgtgcatat ctgatccaaa attaagtttt gatgcaatga cgatcgttgg | 840 |
| aaatctcaac cgagacaacg ctcaagccct ttctaaattt atgagtgtag agccccaaat | 900 |
| aagactttgg gatattcttc aaacaaagtt taaagctaaa gcacttcaag aaaaagttta | 960 |
| tattgaatat gacaaagtga aagcagatag ttgggataga cgtaatatgc gtattgaatt | 1020 |
| taatccaaac aaacttacac gagatgaaat gatttggtta aaacaaaata taataagcta | 1080 |
| catggaagat gacggtttta caagattaga tttagccttt gattttgaag atgatttgag | 1140 |
| tgactactat gcaatgtctg ataaagcagt taagaaaact attttttatg gtcgtaatgg | 1200 |
| taagccagaa acaaaatatt ttggcgtgag agatagtaat agatttatta gaatttataa | 1260 |
| taaaaagcaa gaacgtaaag ataatgcaga tgctgaagtt atgtctgaac atttatggcg | 1320 |
| tgtagaaatc gaacttaaaa gagatatggt ggattactgg aatgattgct ttagtgattt | 1380 |
| acatatcttg caaccagatt ggaaaactat ccaacgcact gcggatagag caatagtttt | 1440 |
| tatgttattg agtgatgaag aagaatgggg aaagcttcac agaaattcta gaacaaaata | 1500 |
| taagaatttg ataaaagaaa tttcgccagt cgatttaacg gacttaatga aatcgacttt | 1560 |

-continued

| SEQUENCES | |
|---|---|
| aaaagcgaac gaaaaacaat tgcaaaaaca aatcgatttt tggcaacatg aatttaaatt | 1620 |
| ttggaaatag tgtacatatt aatattactg aacaaaaatg atatatttaa actattctaa | 1680 |
| tttaggagga tttttttatg aagtgtctat ttaaaaattt ggggaattta tatgaggtga | 1740 |
| aagaataatt taccccctata aactttagtc acctcaagta aagaggtaaa attgtttagt | 1800 |
| ttatataaaa aatttaaagg tttgttttat agcgttttat tttggctttg tattctttca | 1860 |
| ttttttagtg tattaaatga aatggtttta aatgtttctt tacctgatat tgcaaatcat | 1920 |
| tttaatacta ctcctggaat tacaaactgg gtaaacactg catatatgtt aactttttcg | 1980 |
| ataggaacag cagtatatgg aaaattatct gattatataa atataaaaaa attgttaatt | 2040 |
| attggtatta gtttgagctg tcttggttca ttgattgctt ttattgggcc cacctaggaa | 2100 |
| ttgaatgaga catgctacac ctccggataa taaatatata taaacgtata tagatttcat | 2160 |
| aaagtctaac acactagact tatttacttc gtaattaagt cgttaaaccg tgtgctctac | 2220 |
| gaccaaaact ataaaacctt taagaacttt cttttttttac aagaaaaaag aaattagata | 2280 |
| aatctctcat atcttttatt caataatcgc atccgattgc agtataaatt taacgatcac | 2340 |
| tcatcatgtt catatttatc agagctcgtg ctataattat actaatttta taaggaggaa | 2400 |
| aaaatatggg catttttagt atttttgtaa tcagcacagt tcattatcaa ccaaacaaaa | 2460 |
| aataagtggt tataatgaat cgttaataag caaaattcat ataaccaaat taaagagggt | 2520 |
| tataatgaac gagaaaaata taaaacacag tcaaaacttt attacttcaa aacataatat | 2580 |
| agataaaata atgacaaata taagattaaa tgaacatgat aatatctttg aaatcggctc | 2640 |
| aggaaaaggc catttttaccc ttgaattagt aaagaggtgt aatttcgtaa ctgccattga | 2700 |
| aatagaccat aaattatgca aaactacaga aaataaactt gttgatcacg ataatttcca | 2760 |
| agttttaaac aaggatatat tgcagtttaa atttcctaaa aaccaatcct ataaaatata | 2820 |
| tggtaatata ccttataaca taagtacgga tataatacgc aaaattgttt ttgatagtat | 2880 |
| agctaatgag atttatttaa tcgtggaata cgggtttgct aaaagattat taaatacaaa | 2940 |
| acgctcattg gcattacttt taatggcaga agttgatatt tctatattaa gtatggttcc | 3000 |
| aagagaatat tttcatccta aacctaaagt gaatagctca cttatcagat taagtagaaa | 3060 |
| aaaatcaaga atatcacaca aagataaaca aaagtataat tatttcgtta tgaaatgggt | 3120 |
| taacaaagaa tacaagaaaa tatttacaaa aaatcaattt aacaattcct taaaacatgc | 3180 |
| aggaattgac gatttaaaca atattagctt tgaacaattc ttatctcttt tcaatagcta | 3240 |
| taaattattt aataagtaag ttaagggatg cataaactgc atcccttaac ttgtttttcg | 3300 |
| tgtgcctatt ttttgtgaat cgattatgtc ttttgcgcag tcggcttaaa ccagttttcc | 3360 |
| gcggcgctcg agcggccgca tagttaagcc agccccgaca cccgccaaca cccgctgacg | 3420 |
| cgccctgacg ggcttgtctg ctcccggcat ccgcttacag acaagctgtg accgtctccg | 3480 |
| ggagctgcat gtgtcagagg ttttcaccgt catcaccgaa acgcgcgaga cgaaagggcc | 3540 |
| tcgtgatacg cctattttta taggttaatg tcatgataat aatggtttct tagacgtcag | 3600 |
| gtggcacttt tcggggaaat gtgcgcggaa cccctatttg tttatttttc taaatacatt | 3660 |
| caaatatgta tccgctcatg agacaataac cctgataaat gcttcaataa tattgaaaaa | 3720 |
| ggaagagtat gagtattcaa catttccgtg tcgcccttat tccctttttt gcggcatttt | 3780 |
| gccttcctgt ttttgctcac ccagaaacgc tggtgaaagt aaaagatgct gaagatcagt | 3840 |
| tgggtgcacg agtgggttac atcgaactgg atctcaacag cggtaagatc cttgagagtt | 3900 |

-continued

| SEQUENCES |
| --- |
| ttcgccccga agaacgtttt ccaatgatga gcacttttaa agttctgcta tgtggcgcgg 3960 |
| tattatcccg tattgacgcc gggcaagagc aactcggtcg ccgcatacac tattctcaga 4020 |
| atgacttggt tgagtactca ccagtcacag aaaagcatct tacggatggc atgacagtaa 4080 |
| gagaattatg cagtgctgcc ataaccatga gtgataacac tgcggccaac ttacttctga 4140 |
| caacgatcgg aggaccgaag gagctaaccg cttttttgca caacatgggg gatcatgtaa 4200 |
| ctcgccttga tcgttgggaa ccggagctga atgaagccat accaaacgac gagcgtgaca 4260 |
| ccacgatgcc tgtagcaatg gcaacaacgt tgcgcaaact attaactggc gaactactta 4320 |
| ctctagcttc ccggcaacaa ttaatagact ggatggaggc ggataaagtt gcaggaccac 4380 |
| ttctgcgctc ggcccttccg gctggctggt ttattgctga taaatctgga gccggtgagc 4440 |
| gtgggtctcg cggtatcatt gcagcactgg ggccagatgg taagccctcc cgtatcgtag 4500 |
| ttatctacac gacggggagt caggcaacta tggatgaacg aaatagacag atcgctgaga 4560 |
| taggtgcctc actgattaag cattggtaac tgtcagacca agtttactca tatatacttt 4620 |
| agattgattt aaaacttcat ttttaattta aaaggatcta ggtgaagatc ctttttgata 4680 |
| atctcatgac caaaatccct taacgtgagt tttcgttcca ctgagcgtca gaccccgtag 4740 |
| aaaagatcaa aggatcttct tgagatcctt tttttctgcg cgtaatctgc tgcttgcaaa 4800 |
| caaaaaaacc accgctacca gcggtggttt gtttgccgga tcaagagcta ccaactcttt 4860 |
| ttccgaaggt aactggcttc agcagagcgc agataccaaa tactgttctt ctagtgtagc 4920 |
| cgtagttagg ccaccacttc aagaactctg tagcaccgcc tacatacctc gctctgctaa 4980 |
| tcctgttacc agtggctgct gccagtggcg ataagtcgtg tcttaccggg ttggactcaa 5040 |
| gacgatagtt accggataag gcgcagcggt cgggctgaac ggggggttcg tgcacacagc 5100 |
| ccagcttgga gcgaacgacc tacaccgaac tgagatacct acagcgtgag ctatgagaaa 5160 |
| gcgccacgct tcccgaaggg agaaaggcgg acaggtatcc ggtaagcggc agggtcggaa 5220 |
| caggagagcg cacgagggag cttccagggg gaaacgcctg gtatctttat agtcctgtcg 5280 |
| ggtttcgcca cctctgactt gagcgtcgat ttttgtgatg ctcgtcaggg gggcggagcc 5340 |
| tatggaaaaa cgccagcaac gcggcctttt tacggttcct ggccttttgc tggccttttg 5400 |
| ctcacatgtt ctttcctgcg ttatcccctg attctgtgga taaccgtatt accgcctttg 5460 |
| agtgagctgg cggccgctgc atgcctgcag gtcgactcta gaggatcccc cccctgatat 5520 |
| ttttgactaa accaaatgct aacccagaaa tacaatcact gtgtctaatg aataatttgt 5580 |
| tttataaaca ctttttttgtt tacttctcat ttttaattag ttataattaa ctaaataata 5640 |
| gagcattaaa tatatttaat aaaacttatt taatgcaaaa ttatgactaa catatctata 5700 |
| ataaataaag attagatatc aatatattat cgggcaaatg tatcgagcaa gatgcatcgg 5760 |
| atcgatccag gaggtatacc tgattaactt tataaggagg aaaaacatat gagtatcgtt 5820 |
| caagcgaaat ttgaagcaaa agaaacgagt ttccatgtgg aaggatatga gaagatcgag 5880 |
| tacgatttgg tgtatgttga cggcattttt gagatacaaa attctgcgtt ggcggatgta 5940 |
| tatcagggat ttggtagatg cttggcgata gttgatgcga atgtgagtcg tttgtatggt 6000 |
| aatcagatcc aggcgtattt ccaatactat ggtattgagt tacgtttgtt tcctataacg 6060 |
| attacggagc ctgataagac gattcagact ttcgagcgag ttattgacgt ctttgctgac 6120 |
| ttcaagttag tcagaaaaga accagtcttg gtagtgggtg gtggattaat cacagacgta 6180 |

-continued

| SEQUENCES | |
| --- | --- |
| gtaggcttcg cgtgcagtac ttacagaaga tcttctaact acatccgaat accgacaacg | 6240 |
| ttaataggtt tgattgatgc tagtgttgct atcaaggtgg cagtaaatca cagaaaatta | 6300 |
| aagaaccgat tgggagctta ccacgcatca cgaaaagtct tcttagactt ttctttgtta | 6360 |
| cgaacattgc cgactgatca agtcagaaac ggaatggctg aattagtaaa gatcgcggtc | 6420 |
| gtggcacatc aggaggtgtt cgagttgtta gagaagtacg gagaagagtt attacgaacg | 6480 |
| catttcggta atatagacgc tactcctgaa attaaggaga tcgcgcaccg attgacatac | 6540 |
| aaagctattc ataagatgtt agagttggag gttcctaact tacacgagtt ggacttagac | 6600 |
| cgtgtaatag cttatggtca tacgtggagt ccgacattag aattggctcc tcgtttgcct | 6660 |
| atgttccacg gacacgcggt caacgtcgat atggcattca gtgcgacgat tgctgcacga | 6720 |
| cgaggttaca ttacgattgc tgagcgtgat agaatcttag gattaatgag tcgagtcggt | 6780 |
| ttaagtttgg accaccctat gttggatatt gacatcttat ggcgaggtac agaatctatc | 6840 |
| actttaactc gagacggatt attgcgtgct gcaatgccga agcctatagg cgactgtgta | 6900 |
| ttcgtcaatg atttgactcg agaagaattg gcagcagcgt tagcggacca caaagaatta | 6960 |
| tgtacgagtt atccgcgtgg tggtgaaggc gtcgatgtct atccagtata tcaaaaagag | 7020 |
| ttaatcggaa gtgtaaagta acccccctga ttaactttat aaggaggaaa aacatatgtt | 7080 |
| atcaggacat attgaaggac aaactttaaa gatgtttgtt catatgacga aggctaagaa | 7140 |
| ggtattagaa attggaatgt tcacaggcta ctctgcgtta gcgatggcag aggcgttacc | 7200 |
| agaggatggt ttgttagtcg cgtgcgaagt tgatccttac gcagcggaga taggtcaaaa | 7260 |
| ggcattccag caatcaccac acggcggcaa gatacgagtt gagttggacg cagctttagc | 7320 |
| gactttggac aaattagcag aagcaggaga gagttttgat ttggttttca tagacgctga | 7380 |
| caagaaggaa tacgtggctt attttcataa gttgttggga agttcattat tagctccaga | 7440 |
| cggtttcata tgcgttgaca acactttgtt gcaaggagaa gtatatttac cggcggagga | 7500 |
| gcgatcagtg aatggtgagg ctatcgcaca gttcaatcat actgtcgcaa ttgatccgcg | 7560 |
| agtcgagcaa gtgttattgc cgttgagaga tggtttaact attattcgtc gtattcagcc | 7620 |
| ataacccccc tgattaactt tataaggagg aaaaacatat ggctcaatct ttaccattat | 7680 |
| cttctgcacc agcgactccg tcattgccat cacagactaa gattgctgcg atcatccaga | 7740 |
| atatctgtac gttggcgttg ttgttgttgg ctttgccaat taacgctacg atagtgttta | 7800 |
| tcagtttgtt agtatttcga ccacagaagg tgaaggctgc taacccacaa acaatattaa | 7860 |
| tctcaggtgg aaagatgact aaagcattgc agttagcacg atctttccat gcagctggtc | 7920 |
| atagagttgt tttggtggaa acgcataagt attggttgac tggtcacaga ttctcacagg | 7980 |
| cagtagacaa attttatact gtccctgcac cgcaagacaa tccgcaagcg tatattcaag | 8040 |
| ctttggtaga cattgtcaaa caggaaaata tagacgtcta tattccggtg acatctccgg | 8100 |
| tcggctcata ttacgattca ttggcgaagc cggaattgtc tcactattgt gaagtgtttc | 8160 |
| acttcgatgc agacataaca caaatgttag acgacaaatt tgctttaact caaaaagcac | 8220 |
| gatctttggg cttgtcagtc ccgaagtctt tcaaaataac ttctccggag caagtaatta | 8280 |
| acttcgactt ctcaggagaa actagaaaat acatcttaaa aagtattcca tacgacagtg | 8340 |
| tacgtcgttt agatttgaca aagttacctt gtgctacgcc ggaagagaca gcagctttcg | 8400 |
| ttagaagttt gccgatcacg ccagagaagc cgtggataat gcaggaattt ataccaggca | 8460 |
| aggaattttg tacacactca actgtcagaa acggagaatt acgtttgcac tgctgttgtg | 8520 |

-continued

| SEQUENCES | |
|---|---|
| agtcatcagc tttccaagtc aactatgaga acgtaaacaa tccgcagata acagaatggg | 8580 |
| tccaacattt tgtcaaagag ttaaagttga ctggacaaat ctctttcgat ttcatacaag | 8640 |
| ctgaagatgg aacagtatac gctattgagt gtaaccctcg aactcattca gcgataacta | 8700 |
| ctttctatga ccatccgcaa gttgcagaag cttacttgtc acaggctcca acaacggaga | 8760 |
| caattcaacc attaacaaca tctaaaccaa cttattggac atatcatgaa gtgtggagat | 8820 |
| taacgggtat ccgaagtttc actcagttgc aacgatggtt gggcaacatt tggcgtggca | 8880 |
| ctgatgcgat ttaccaaccg gacgacccgt tacctttctt gatggttcat cattggcaaa | 8940 |
| ttccgttgtt attgttgaat aatttgcgac gattaaaggg ttggacacgt attgatttca | 9000 |
| acattggaaa attggtcgaa ttaggaggtg actagccccc ctgattaact ttataaggag | 9060 |
| gaaaaacata tgcagacgat tgattttaat atccgaaagt tgttagtgga atggaacgcg | 9120 |
| acacatcgtg attacgactt gtcacagtct ttgcacgaat tgatagttgc acaagttgaa | 9180 |
| agaactcctg aagctattgc tgttacgttc gacaagcagc aattaacgta tcaggaatta | 9240 |
| aatcataaag cgaaccagtt gggacactac ttacaaacgt taggtgtcca accggagacg | 9300 |
| ttagtcggtg tctgtttgga acgtagtttg gagatggtca tttgtttatt aggaatattg | 9360 |
| aaggcgggcg gtgcttatgt ccctatcgac ccggaatatc ctcaggaacg tatagcttac | 9420 |
| atgttagaag actctcaggt gaaggttttg ttgactcaag aaaaattatt aaatcagatc | 9480 |
| ccgcaccatc aggcacaaac aatatgtgtt gatagagaat gggagaaaat ctctacacaa | 9540 |
| gcgaatacaa atccgaaatc aaatattaag acggataact tggcatacgt catttacact | 9600 |
| tctggtagta caggaaaacc aaaaggtgcg atgaacacgc ataaaggcat atgtaatcga | 9660 |
| ttattgtgga tgcaagaggc ttatcagatc gatagtacgg acagtatctt gcaaaaaacg | 9720 |
| ccgttctctt ttgatgtttc agtctgggag tttttctgga cattattgac gggagcgcga | 9780 |
| ttggttatcg ctaagccagg aggccacaaa gacagtgcat atttgataga tttgataaca | 9840 |
| caggagcaaa ttacaacttt acactttgtg ccgtcaatgt tacaagtctt cttacagaac | 9900 |
| cgtcacgtaa gtaagtgtag ttctttaaag cgagtcattt gctcaggaga ggcgttatca | 9960 |
| attgatttac agaatagatt tttccaacac ttgcagtgtg agttgcacaa cttatatggt | 10020 |
| ccaacagaag ctgctattga cgtaactttt tggcaatgta gaaaggattc taatttaaaa | 10080 |
| tctgtcccga taggtagacc tatagcgaat acacaaatat atatcttgga cgctgattta | 10140 |
| cagccggtta acataggcgt aacgggagag atttatattg gaggtgtagg cgtggctcgt | 10200 |
| ggatatttga ataaagagga gttaactaaa gaaaaattca tcatcaatcc tttcccaaac | 10260 |
| tctgaattca aacgtttgta taaaacgggc gatttagcgc gttatttacc agacggcaac | 10320 |
| atagaatatt tgggcagaac agattatcaa gtgaaaatac gaggctatag aatagaaata | 10380 |
| ggcgaaatag agaacgtctt gtctagtcat ccacaggtga gagaagctgt cgtaatagct | 10440 |
| agagatgata acgcgcaaga gaaacagatc atcgcttaca tcacatataa tagtatcaag | 10500 |
| ccgcaattgg acaacttacg agacttcttg aaggcacgtt tgccggattt tatgattcct | 10560 |
| gcagcttttg tgatgttgga acacttaccg ttgactccaa gtggcaaagt agatcgaaag | 10620 |
| gcattgccta agccagattt attcaattac tcagaacata attcttatgt tgcaccgcgt | 10680 |
| aatgaagtag aggaaaaatt ggtgcagata tggtctaaca ttttacattt acctaaagta | 10740 |
| ggcgttactg aaaacttttt cgcgatcggt ggtaatagtt tgaaggcgtt acacttaatt | 10800 |

-continued

| SEQUENCES | |
|---|---|
| agtcagattg aggaattatt cgcaaaggag attagtttgg cgacgttgtt gacaaatcca | 10860 |
| gttattgcgg acttagctaa agttattcaa gcgaataacc aaatccacaa ttcaccatta | 10920 |
| gtgccgatcc aaccgcaggg caagcagcaa ccttttttct gtatccatcc ggcgggtgga | 10980 |
| catgtattat gttacttcaa gttggcgcaa tacataggaa cggaccaacc attttacggc | 11040 |
| ttgcaggctc aaggttttta cggagatgaa gcgccattga cacgtgttga ggatatggca | 11100 |
| tctttgtacg tgaaaacgat acgagagttc caacctcaag gcccgtaccg agtcggtggc | 11160 |
| tggtctttcg gcggcgtagt ggcgtacgag gtcgcgcaac aattgcatcg acaaggacaa | 11220 |
| gaggtctcat tgttagcaat tttagatagt tatgtgccaa tcttattgga taaacaaaag | 11280 |
| ccaatcgatg atgtgtactt ggtgggagtc ttgtctcgtg tcttcggtgg aatgttcggt | 11340 |
| caagacaatt tagtaacacc tgaagaaatc gaaaatttga cggtagaaga gaaaatcaat | 11400 |
| tacatcattg ataaagctag atcagcacgt atttttcctc cgggagtaga acgacagaac | 11460 |
| aatcgtcgta ttttggatgt cttagtgggc actttgaaag caacttatag ttacattcga | 11520 |
| cagccttatc cgggcaaggt cacagttttc cgtgcgcgtg aaaaacatat aatggcgccg | 11580 |
| gacccaactt tggtctgggt tgaattattt tcagttatgg cggcgcagga aataaagatc | 11640 |
| atagacgtac cgggcaatca ctactctttt gtcttagaac cacatgtaca agtattggct | 11700 |
| cagagattac aggactgctt agaaaataac tcatgacccg ggtaccgagc tcgaattcag | 11760 |
| gcgcgcctat tctaaatgca taataaatac tgataacatc ttatattttg tattatattt | 11820 |
| tgtattatcg ttgacatgta taattttgat atcaaaaact gattttccct ctattatttt | 11880 |
| cgagatttat tttcttaatt ctctttaaca aactagaaat attgtatata caaaaaatta | 11940 |
| taaataatag atgaatagtt taattatagg tgttcatcaa tcgaaaaagc aacgtatctt | 12000 |
| atttaaagtg cgttgctttt ttctcattta taaggttaaa taattctcat atatcaagca | 12060 |
| aagtgacagg cg | 12072 |
| SEQ ID NO: 6 | |
| cccctgatat ttttgactaa accaaatgct aacccagaaa tacaatcact gtgtctaatg | 60 |
| aataatttgt tttataaaca ctttttgtt tacttctcat ttttaattag ttataattaa | 120 |
| ctaaataata gagcattaaa tatatttaat aaaacttatt taatgcaaaa ttatgactaa | 180 |
| catatctata ataaataaag attagatatc aatatattat cgggcaaatg tatcgagcaa | 240 |
| gatgcatcgg atcgatccag gaggtatacc tgattaactt tataaggagg aaaaacatat | 300 |
| gagtatcgtt caagcgaaat ttgaagcaaa agaaacgagt ttccatgtgg aaggatatga | 360 |
| gaagatcgag tacgatttgg tgtatgttga cggcattttt gagatacaaa attctgcgtt | 420 |
| ggcggatgta tatcagggat ttggtagatg cttggcgata gttgatgcga atgtgagtcg | 480 |
| tttgtatggt aatcagatcc aggcgtattt ccaatactat ggtattgagt tacgtttgtt | 540 |
| tcctataacg attacggagc ctgataagac gattcagact ttcgagcgag ttattgacgt | 600 |
| ctttgctgac ttcaagttag tcagaaaaga accagtcttg gtagtgggtg gtggattaat | 660 |
| cacagacgta gtaggcttcg cgtgcagtac ttacagaaga tcttctaact acatccgaat | 720 |
| accgacaacg ttaataggtt tgattgatgc tagtgttgct atcaaggtgg cagtaaatca | 780 |
| cagaaaatta aagaaccgat tgggagctta ccacgcatca cgaaaagtct tcttagactt | 840 |
| ttctttgtta cgaacattgc cgactgatca agtcagaaac ggaatggctg aattagtaaa | 900 |
| gatcgcggtc gtggcacatc aggaggtgtt cgagttgtta gagaagtacg gagaagagtt | 960 |

-continued

| SEQUENCES | |
|---|---|
| attacgaacg catttcggta atatagacgc tactcctgaa attaaggaga tcgcgcaccg | 1020 |
| attgacatac aaagctattc ataagatgtt agagttggag gttcctaact tacacgagtt | 1080 |
| ggacttagac cgtgtaatag cttatggtca tacgtggagt ccgacattag aattggctcc | 1140 |
| tcgtttgcct atgttccacg gacacgcggt caacgtcgat atggcattca gtgcgacgat | 1200 |
| tgctgcacga cgaggttaca ttacgattgc tgagcgtgat agaatcttag gattaatgag | 1260 |
| tcgagtcggt ttaagtttgg accaccctat gttggatatt gacatcttat ggcgaggtac | 1320 |
| agaatctatc actttaactc gagacggatt attgcgtgct gcaatgccga agcctatagg | 1380 |
| cgactgtgta ttcgtcaatg atttgactcg agaagaattg gcagcagcgt tagcggacca | 1440 |
| caaagaatta tgtacgagtt atccgcgtgg tggtgaaggc gtcgatgtct atccagtata | 1500 |
| tcaaaaagag ttaatcggaa gtgtaaagta accc | 1534 |
| SEQ ID NO: 7 | |
| ccctgattaa ctttataagg aggaaaaaca tatgttatca ggacatattg aaggacaaac | 60 |
| tttaaagatg tttgttcata tgacgaaggc taagaaggta ttagaaattg gaatgttcac | 120 |
| aggctactct gcgttagcga tggcagaggc gttaccagag gatggtttgt tagtcgcgtg | 180 |
| cgaagttgat ccttacgcag cggagatagg tcaaaaggca ttccagcaat caccacacgg | 240 |
| cggcaagata cgagttgagt tggacgcagc tttagcgact ttggacaaat tagcagaagc | 300 |
| aggagagagt tttgatttgg ttttcataga cgctgacaag aaggaatacg tggcttattt | 360 |
| tcataagttg ttgggaagtt cattattagc tccagacggt ttcatatgcg ttgacaacac | 420 |
| tttgttgcaa ggagaagtat atttaccggc ggaggagcga tcagtgaatg gtgaggctat | 480 |
| cgcacagttc aatcatactg tcgcaattga tccgcgagtc gagcaagtgt tattgccgtt | 540 |
| gagagatggt ttaactatta ttcgtcgtat tcagccataa ccc | 583 |
| SEQ ID NO: 8 | |
| ccctgattaa ctttataagg aggaaaaaca tatggctcaa tctttaccat tatcttctgc | 60 |
| accagcgact ccgtcattgc catcacagac taagattgct gcgatcatcc agaatatctg | 120 |
| tacgttggcg ttgttgttgt tggctttgcc aattaacgct acgatagtgt ttatcagttt | 180 |
| gttagtattt cgaccacaga aggtgaaggc tgctaaccca caaacaatat taatctcagg | 240 |
| tggaaagatg actaaagcat tgcagttagc acgatctttc catgcagctg gtcatagagt | 300 |
| tgttttggtg gaaacgcata agtattggtt gactggtcac agattctcac aggcagtaga | 360 |
| caaattttat actgtccctg caccgcaaga caatccgcaa gcgtatattc aagctttggt | 420 |
| agacattgtc aaacaggaaa atatagacgt ctatattccg gtgacatctc cggtcggctc | 480 |
| atattacgat tcattggcga agccggaatt gtctcactat tgtgaagtgt ttcacttcga | 540 |
| tgcagacata acacaaatgt tagacgacaa atttgcttta actcaaaaag cacgatcttt | 600 |
| gggcttgtca gtcccgaagt ctttcaaaat aacttctccg gagcaagtaa ttaacttcga | 660 |
| cttctcagga gaaactagaa aatacatctt aaaaagtatt ccatacgaca gtgtacgtcg | 720 |
| tttagatttg acaaagttac cttgtgctac gccggaagag acagcagctt tcgttagaag | 780 |
| tttgccgatc acgccagaga agccgtggat aatgcaggaa tttataccag gcaaggaatt | 840 |
| ttgtacacac tcaactgtca gaaacggaga attacgtttg cactgctgtt gtgagtcatc | 900 |
| agctttccaa gtcaactatg agaacgtaaa caatccgcag ataacagaat gggtccaaca | 960 |
| ttttgtcaaa gagttaaagt tgactggaca aatctctttc gatttcatac aagctgaaga | 1020 |
| tggaacagta tacgctattg agtgtaaccc tcgaactcat tcagcgataa ctactttcta | 1080 |

-continued

| SEQUENCES |
| --- |
| tgaccatccg caagttgcag aagcttactt gtcacaggct ccaacaacgg agacaattca 1140 |
| accattaaca acatctaaac caacttattg gacatatcat gaagtgtgga gattaacggg 1200 |
| tatccgaagt ttcactcagt tgcaacgatg gttgggcaac atttggcgtg gcactgatgc 1260 |
| gatttaccaa ccggacgacc cgttaccttt cttgatggtt catcattggc aaattccgtt 1320 |
| gttattgttg aataatttgc gacgattaaa gggttggaca cgtattgatt tcaacattgg 1380 |
| aaaattggtc gaattaggag gtgactagcc c 1411 |
| SEQ ID NO: 9 |
| ccctgattaa ctttataagg aggaaaaaca tatgcagacg attgatttta atatccgaaa 60 |
| gttgttagtg gaatggaacg cgacacatcg tgattacgac ttgtcacagt ctttgcacga 120 |
| attgatagtt gcacaagttg aaagaactcc tgaagctatt gctgttacgt tcgacaagca 180 |
| gcaattaacg tatcaggaat taaatcataa agcgaaccag ttgggacact acttacaaac 240 |
| gttaggtgtc caaccggaga cgttagtcgg tgtctgtttg gaacgtagtt tggagatggt 300 |
| catttgttta ttaggaatat tgaaggcggg cggtgcttat gtccctatcg acccggaata 360 |
| tcctcaggaa cgtatagctt acatgttaga agactctcag gtgaaggttt tgttgactca 420 |
| agaaaaatta ttaaatcaga tcccgcacca tcaggcacaa acaatatgtg ttgatagaga 480 |
| atgggagaaa atctctacac aagcgaatac aaatccgaaa tcaaatatta agacggataa 540 |
| cttggcatac gtcatttaca cttctggtag tacaggaaaa ccaaaaggtg cgatgaacac 600 |
| gcataaaggc atatgtaatc gattattgtg gatgcaagag gcttatcaga tcgatagtac 660 |
| ggacagtatc ttgcaaaaaa cgccgttctc ttttgatgtt tcagtctggg agtttttctg 720 |
| gacattattg acgggagcgc gattggttat cgctaagcca ggaggccaca aagacagtgc 780 |
| atatttgata gatttgataa cacaggagca aattacaact ttacactttg tgccgtcaat 840 |
| gttacaagtc ttcttacaga accgtcacgt aagtaagtgt agttctttaa agcgagtcat 900 |
| ttgctcagga gaggcgttat caattgattt acagaataga tttttccaac acttgcagtg 960 |
| tgagttgcac aacttatatg gtccaacaga agctgctatt gacgtaactt tttggcaatg 1020 |
| tagaaaggat tctaatttaa aatctgtccc gataggtaga cctatagcga atacacaaat 1080 |
| atatatcttg gacgctgatt tacagccggt taacataggc gtaacgggag agatttatat 1140 |
| tggaggtgta ggcgtggctc gtggatattt gaataaagag gagttaacta aagaaaaatt 1200 |
| catcatcaat cctttcccaa actctgaatt caaacgtttg tataaaacgg gcgatttagc 1260 |
| gcgttattta ccagacggca acatagaata tttgggcaga acagattatc aagtgaaaat 1320 |
| acgaggctat agaatagaaa taggcgaaat agagaacgtc ttgtctagtc atccacaggt 1380 |
| gagagaagct gtcgtaatag ctagagatga taacgcgcaa gagaaacaga tcatcgctta 1440 |
| catcacatat aatagtatca agccgcaatt ggacaactta cgagacttct tgaaggcacg 1500 |
| tttgccggat tttatgattc ctgcagcttt tgtgatgttg gaacacttac cgttgactcc 1560 |
| aagtggcaaa gtagatcgaa aggcattgcc taagccagat ttattcaatt actcagaaca 1620 |
| taattcttat gttgcaccgc gtaatgaagt agaggaaaaa ttggtgcaga tatggtctaa 1680 |
| cattttacat ttacctaaag taggcgttac tgaaaacttt ttcgcgatcg gtggtaatag 1740 |
| tttgaaggcg ttacacttaa ttagtcagat tgaggaatta ttcgcaaagg agattagttt 1800 |
| ggcgacgttg ttgacaaatc cagttattgc ggacttagct aaagttattc aagcgaataa 1860 |
| ccaaatccac aattcaccat tagtgccgat ccaaccgcag ggcaagcagc aaccttttt 1920 |

-continued

| SEQUENCES | |
|---|---|
| ctgtatccat ccggcgggtg gacatgtatt atgttacttc aagttggcgc aatacatagg | 1980 |
| aacggaccaa ccattttacg gcttgcaggc tcaaggtttt tacggagatg aagcgccatt | 2040 |
| gacacgtgtt gaggatatgg catctttgta cgtgaaaacg atacgagagt tccaacctca | 2100 |
| aggcccgtac cgagtcggtg gctggtcttt cggcggcgta gtggcgtacg aggtcgcgca | 2160 |
| acaattgcat cgacaaggac aagaggtctc attgttagca attttagata gttatgtgcc | 2220 |
| aatcttattg gataaacaaa agccaatcga tgatgtgtac ttggtgggag tcttgtctcg | 2280 |
| tgtcttcggt ggaatgttcg gtcaagacaa tttagtaaca cctgaagaaa tcgaaaattt | 2340 |
| gacggtagaa gagaaaatca attacatcat tgataaagct agatcagcac gtatttttcc | 2400 |
| tccgggagta gaacgacaga acaatcgtcg tattttggat gtcttagtgg gcactttgaa | 2460 |
| agcaacttat agttacattc gacagcctta tccgggcaag gtcacagttt tccgtgcgcg | 2520 |
| tgaaaaacat ataatggcgc cggacccaac tttggtctgg gttgaattat tttcagttat | 2580 |
| ggcggcgcag gaaataaaga tcatagacgt accgggcaat cactactctt ttgtcttaga | 2640 |
| accacatgta caagtattgg ctcagagatt acaggactgc ttagaaaata actcatgacc | 2700 |
| c | 2701 |

What is claimed is:

1. A genetically modified strain of commensal bacteria which produces a material with UV absorbing properties wherein the commensal bacteria comprises one or more of the nucleotide sequences shown in SEQ ID NO: 6, SEQ ID NO:7, SEQ ID NO:8, and SEQ ID NO:9.

2. A genetically modified strain of commensal bacteria which produces a material with UV absorbing properties wherein the commensal bacteria comprises the nucleotide sequence shown in SEQ ID NO:5.

3. A topical composition comprising the genetically modified strain of commensal bacteria of claim 1 wherein the bacteria is present in a topical composition at a concentration of at least 0.1% by weight of the total composition.

4. A composition comprising the genetically modified strain of commensal bacteria of claim 1 and a sunscreen.

5. The genetically modified strain of commensal bacteria of claim 1 wherein the material with UV absorbing properties is a mycosporine-like amino acid.

6. The genetically modified strain of commensal bacteria of claim 5 wherein the mycosporine-like amino acid is shinorine.

7. A topical composition comprising the genetically modified strain of commensal bacteria of claim 1 wherein the bacteria is present in a topical composition at a concentration of at least 0.1% by weight of the total composition.

8. A composition comprising the genetically modified strain of commensal bacteria of claim 1 and a sunscreen.

9. The genetically modified strain of commensal bacteria of claim 2 wherein the material with UV absorbing properties is a mycosporine-like amino acid.

10. The genetically modified strain of commensal bacteria of claim 9 wherein the mycosporine-like amino acid is shinorine.

11. A topical composition comprising the genetically modified strain of commensal bacteria of claim 2 wherein the bacteria is present in a topical composition at a concentration of at least 0.1% by weight of the total composition.

12. A composition comprising the genetically modified strain of commensal bacteria of claim 2 and a sunscreen.

* * * * *